United States Patent
Clancy et al.

(10) Patent No.: US 10,292,786 B2
(45) Date of Patent: May 21, 2019

(54) RATCHET-SLIDE HANDLE AND SYSTEM FOR FIDUCIAL DEPLOYMENT

(71) Applicant: Cook Medical Technologies LLC, Bloomington, IN (US)

(72) Inventors: Michael Clancy, Co. Limerick (IE); Darach McGrath, Co. Tipperary (IE); Ciaran Toomey, Co. Cork (IE); Triona Campbell, Co. Clare (IE); Patrick Mulcahy, Co. Tipperary (IE); Fionan Keady, Co. Galway (IE)

(73) Assignee: Cook Medical Technologies LLC, Bloomington, IN (US)

( * ) Notice: Subject to any disclaimer, the term of this patent is extended or adjusted under 35 U.S.C. 154(b) by 201 days.

(21) Appl. No.: 15/348,645

(22) Filed: Nov. 10, 2016

(65) Prior Publication Data
US 2017/0056124 A1   Mar. 2, 2017

Related U.S. Application Data

(62) Division of application No. 14/180,022, filed on Feb. 13, 2014, now Pat. No. 9,522,264.
(Continued)

(51) Int. Cl.
*A61B 90/00* (2016.01)
*A61B 17/34* (2006.01)
(Continued)

(52) U.S. Cl.
CPC .......... *A61B 90/39* (2016.02); *A61B 17/3468* (2013.01); *A61M 25/013* (2013.01);
(Continued)

(58) Field of Classification Search
CPC ....... A61M 37/0069; A61B 2090/3987; A61B 2017/00371; A61B 2017/00384; A61B 2017/00407; A61B 17/3468
See application file for complete search history.

(56) References Cited

U.S. PATENT DOCUMENTS

| | | | |
|---|---|---|---|
| 2,009,393 | A | 7/1936 | Failla |
| 2,239,963 | A | 4/1941 | Hoffert |

(Continued)

FOREIGN PATENT DOCUMENTS

| | | |
|---|---|---|
| EP | 0 093 101 A2 | 11/1983 |
| EP | 1 518 549 A1 | 3/2005 |

(Continued)

OTHER PUBLICATIONS

Ammar et al., "Fiducial placement for sterotactic radiation by using EUS feasibility when using a marker compatible with a standard 22-gauge needle," Gastrointestinal Endoscopy, vol. 71, No. 3, pp. 630-633, www.giejournal.org, St. Louis, MO 20210.
(Continued)

*Primary Examiner* — Thaddeus B Cox
(74) *Attorney, Agent, or Firm* — Brinks Gilson & Lione

(57) ABSTRACT

Embodiments include a fiducial deployment system with a handle configured for actuation of same. A fiducial may include one or more protuberances configured to engage one or more slots in a needle of the system. The needle may be configured to deliver a plurality of fiducials to a target location in serial fashion, one at a time. The handle includes an actuation mechanism with a recessible-toothed rack and actuation member(s) configured for incrementally or otherwise controlledly deploying one or more fiducials at a time by advancing a stylet through and/or retracting the body of a slotted needle in which fiducials are disposed with a fiducial protrusion extending into the needle slot, which needle slot also includes retaining structures that do not impede the needle lumen.

11 Claims, 14 Drawing Sheets

Related U.S. Application Data

(60) Provisional application No. 61/769,295, filed on Feb. 26, 2013.

(51) Int. Cl.
*A61M 37/00* (2006.01)
*A61M 25/01* (2006.01)
*A61B 17/00* (2006.01)

(52) U.S. Cl.
CPC .............. *A61M 37/0069* (2013.01); *A61B 2017/00407* (2013.01); *A61B 2090/3987* (2016.02)

(56) References Cited

U.S. PATENT DOCUMENTS

| | | | |
|---|---|---|---|
| 2,269,963 A | 1/1942 | Wappler | |
| 2,410,643 A | 11/1946 | Fielding | |
| 2,620,796 A | 12/1952 | Eriksen et al. | |
| 3,470,834 A | 10/1969 | Bone | |
| 3,815,798 A | 6/1974 | Lavitch et al. | |
| 3,820,545 A | 6/1974 | Jefferts | |
| 4,086,914 A | 5/1978 | Moore | |
| 4,105,030 A | 8/1978 | Kercso | |
| 4,154,239 A | 5/1979 | Turley | |
| 4,451,254 A | 5/1984 | Dinius et al. | |
| 4,646,740 A | 3/1987 | Peters et al. | |
| 4,648,542 A | 3/1987 | Fox et al. | |
| 4,661,103 A | 4/1987 | Harman | |
| 4,700,692 A | 10/1987 | Baumgartner | |
| 4,716,901 A | 1/1988 | Jackson et al. | |
| 4,807,628 A | 2/1989 | Peters et al. | |
| 4,976,686 A | 12/1990 | Ball et al. | |
| 5,002,548 A | 3/1991 | Campbell et al. | |
| 5,024,727 A | 6/1991 | Campbell et al. | |
| 5,047,038 A | 9/1991 | Peters et al. | |
| 5,281,197 A | 1/1994 | Arias et al. | |
| 5,669,543 A | 9/1997 | Ueno | |
| 5,755,726 A | 5/1998 | Pratt et al. | |
| 5,810,769 A | 9/1998 | Schlegel et al. | |
| 5,860,909 A | 1/1999 | Mich et al. | |
| 6,004,320 A | 12/1999 | Casscells et al. | |
| 6,186,144 B1 | 2/2001 | Davis et al. | |
| 6,210,315 B1 | 4/2001 | Andrews et al. | |
| 6,220,248 B1 | 4/2001 | Voegele et al. | |
| 6,221,003 B1 | 4/2001 | Sierocuk et al. | |
| 6,228,055 B1 | 5/2001 | Foerster et al. | |
| 6,264,599 B1 | 7/2001 | Slater et al. | |
| 6,267,718 B1 | 7/2001 | Vitali et al. | |
| 6,270,472 B1 * | 8/2001 | Antaki ............... | A61M 37/0069 600/7 |
| 6,283,948 B1 | 9/2001 | McKernan et al. | |
| 6,347,241 B2 | 2/2002 | Burbank et al. | |
| 6,402,677 B1 | 6/2002 | Jacobs | |
| 6,432,035 B1 | 8/2002 | Ravins et al. | |
| 6,450,938 B1 | 9/2002 | Miller | |
| 6,569,077 B2 | 5/2003 | Schmidt | |
| 6,592,508 B1 | 7/2003 | Ravins et al. | |
| 6,613,002 B1 | 9/2003 | Clark et al. | |
| 6,796,935 B1 | 9/2004 | Savino | |
| 6,824,507 B2 | 11/2004 | Miller | |
| 6,837,844 B1 | 1/2005 | Ellard et al. | |
| 6,889,833 B2 | 5/2005 | Seiler et al. | |
| 7,001,341 B2 | 2/2006 | Gellman et al. | |
| 7,008,368 B2 | 3/2006 | Terwilliger et al. | |
| 7,041,048 B2 | 5/2006 | Drobnik et al. | |
| 7,083,566 B2 | 8/2006 | Tornes et al. | |
| 7,104,945 B2 | 9/2006 | Miller | |
| 7,144,386 B2 | 12/2006 | Korkor et al. | |
| 7,214,206 B2 | 5/2007 | Rue et al. | |
| 7,247,160 B2 | 7/2007 | Seiler et al. | |
| 7,280,865 B2 | 10/2007 | Adler | |
| 7,335,155 B2 | 2/2008 | Chu | |
| 7,361,135 B2 | 4/2008 | Drobnik et al. | |
| 7,407,054 B2 | 8/2008 | Seiler et al. | |
| 7,429,240 B2 | 9/2008 | Miller | |
| 7,465,279 B2 | 12/2008 | Beckman et al. | |
| 7,510,549 B2 | 3/2009 | Rue et al. | |
| 7,565,191 B2 | 7/2009 | Burbank et al. | |
| 7,577,473 B2 | 8/2009 | Davis et al. | |
| 7,588,528 B2 | 9/2009 | Drobnik et al. | |
| 7,615,076 B2 | 11/2009 | Cauthen, II et al. | |
| 7,651,505 B2 | 1/2010 | Lubock et al. | |
| 7,736,343 B2 | 6/2010 | Marshall et al. | |
| 7,819,820 B2 | 10/2010 | Field et al. | |
| 7,850,639 B2 | 12/2010 | Rue et al. | |
| 2003/0120141 A1 | 6/2003 | Adler | |
| 2003/0233101 A1 | 12/2003 | Lubock et al. | |
| 2003/0233126 A1 | 12/2003 | Kaplan et al. | |
| 2004/0097780 A1 | 5/2004 | Otsuka | |
| 2004/0236213 A1 | 11/2004 | Jones et al. | |
| 2004/0260199 A1 | 12/2004 | Hardia, Jr. et al. | |
| 2005/0038355 A1 | 2/2005 | Gellman et al. | |
| 2005/0267319 A1 | 12/2005 | White et al. | |
| 2006/0058569 A1 | 3/2006 | Chu | |
| 2006/0173236 A1 | 8/2006 | White et al. | |
| 2006/0184090 A1 | 8/2006 | Davis et al. | |
| 2006/0235298 A1 | 10/2006 | Kotmel et al. | |
| 2007/0093726 A1 | 4/2007 | Leopold et al. | |
| 2007/0167736 A1 | 7/2007 | Dietz et al. | |
| 2007/0270640 A1 | 11/2007 | Dimitriou et al. | |
| 2008/0033280 A1 | 2/2008 | Lubock et al. | |
| 2008/0033286 A1 | 2/2008 | Whitmore et al. | |
| 2008/0243148 A1 | 10/2008 | Mikkaichi et al. | |
| 2008/0269688 A1 | 10/2008 | Colucci et al. | |
| 2008/0287782 A1 | 11/2008 | Traboulsi et al. | |
| 2009/0018439 A1 | 1/2009 | Jones et al. | |
| 2009/0105518 A1 | 4/2009 | Schreiber et al. | |
| 2009/0105584 A1 | 4/2009 | Jones | |
| 2009/0131734 A1 | 5/2009 | Neustadter et al. | |
| 2009/0209804 A1 | 8/2009 | Seiler et al. | |
| 2009/0227893 A1 | 9/2009 | Coonahan et al. | |
| 2010/0010342 A1 | 1/2010 | Burbank et al. | |
| 2010/0036241 A1 | 2/2010 | Mayse et al. | |
| 2010/0042041 A1 | 2/2010 | Tune et al. | |
| 2010/0063392 A1 | 3/2010 | Nishina et al. | |
| 2010/0137891 A1 | 6/2010 | Shalon et al. | |
| 2010/0280367 A1 | 11/2010 | Ducharme et al. | |
| 2010/0331677 A1 | 12/2010 | Hong et al. | |
| 2011/0028831 A1 | 2/2011 | Kent | |
| 2011/0071424 A1 | 3/2011 | Nock et al. | |
| 2011/0152611 A1 | 6/2011 | Ducharme et al. | |
| 2011/0282296 A1 | 11/2011 | Harms et al. | |
| 2011/0288581 A1 | 11/2011 | Paul, Jr. et al. | |
| 2012/0265042 A1 | 10/2012 | Neinast et al. | |
| 2013/0006101 A1 | 1/2013 | McHugo et al. | |
| 2013/0006286 A1 | 1/2013 | Lavelle et al. | |
| 2013/0096427 A1 | 4/2013 | Murray et al. | |
| 2013/0178822 A1 * | 7/2013 | Hickingbotham ............ | A61B 17/3468 604/506 |
| 2014/0121677 A1 | 5/2014 | Clancy et al. | |

FOREIGN PATENT DOCUMENTS

| | | |
|---|---|---|
| EP | 2 719 355 A2 | 4/2014 |
| FR | 2 762 517 A1 | 4/1997 |
| JP | 6323312 | 11/1994 |
| WO | WO 97/19724 A1 | 6/1997 |
| WO | WO 01/00101 A1 | 1/2001 |
| WO | WO 2007/094001 A2 | 8/2007 |
| WO | WO 2007/103204 A2 | 9/2007 |
| WO | WO 2008/016551 A1 | 2/2008 |
| WO | WO 2009/100106 A1 | 8/2009 |
| WO | WO 2009/132349 A2 | 10/2009 |
| WO | WO 2010/126750 A2 | 11/2010 |
| WO | WO 2012/152666 A1 | 11/2012 |
| WO | WO 2014/133777 A1 | 9/2014 |

OTHER PUBLICATIONS

Classen et al. "Gastroenterological Endoscopy," EUS-Guided Implantation of Radiopaque Markers (Fiducials), p. 475.

(56) References Cited

OTHER PUBLICATIONS

DiMaio et al., "EUS-guided fiducial placement for image-guided radiation therapy in GI malignancies by using a 22-gauge needle (with videos),"Gastrointestinal Endoscopy, vol. 71, No. 7, pp. 1204-1210.
International Search Report for International Application No. PCT/US2010/059641, dated May 25, 2011, 5 pages.
International Search Report for International Application No. PCT/US2012/058679, dated Jan. 2, 2013, 3 pages.
International Search Report for International Application No. PCT/US2013/023401, dated May 7, 2013, 2 pages.
International Search Report for International Application No. PCT/US2014/016218, dated Apr. 4, 2014, 3 pages.
Marker Kit, "Gold fiducial markers—Accurate localization for soft tissue targets," Best Medical International, Inc. Springfield, VA, Jan. 2008, pp. 42-54.
PCT Notification of Transmittal of the International Search Report and Written Opinion of the International Search Authority, or the Declaration for PCT Application No. PCT/US2010/031842, dated May 6, 2010.
Specification of U.S. Appl. No. 62/009,587.
Specification of U.S. Appl. No. 62/012,789.

\* cited by examiner

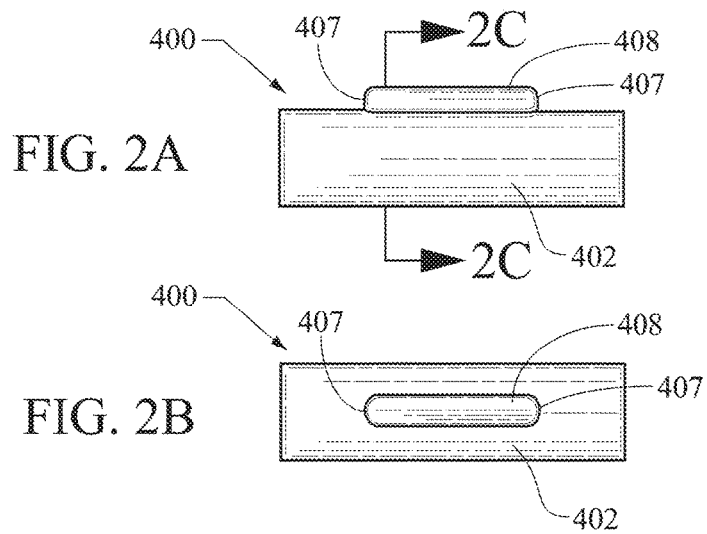
FIG. 2A
FIG. 2B
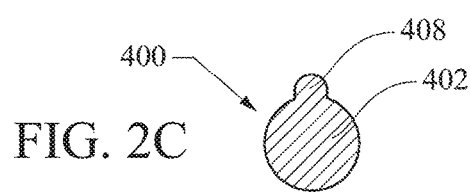
FIG. 2C
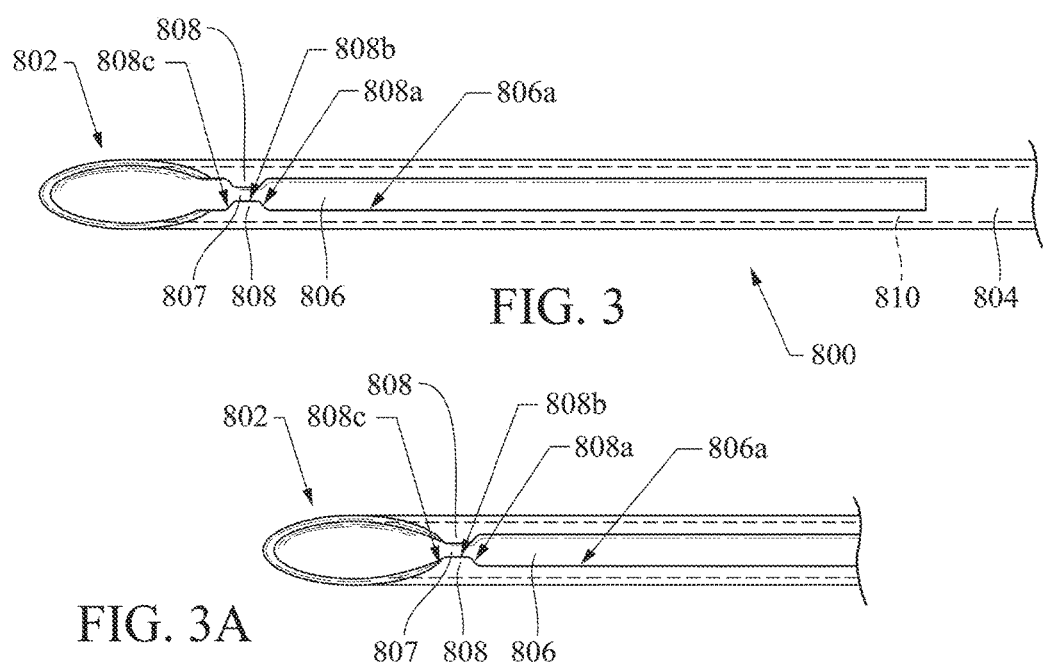
FIG. 3
FIG. 3A

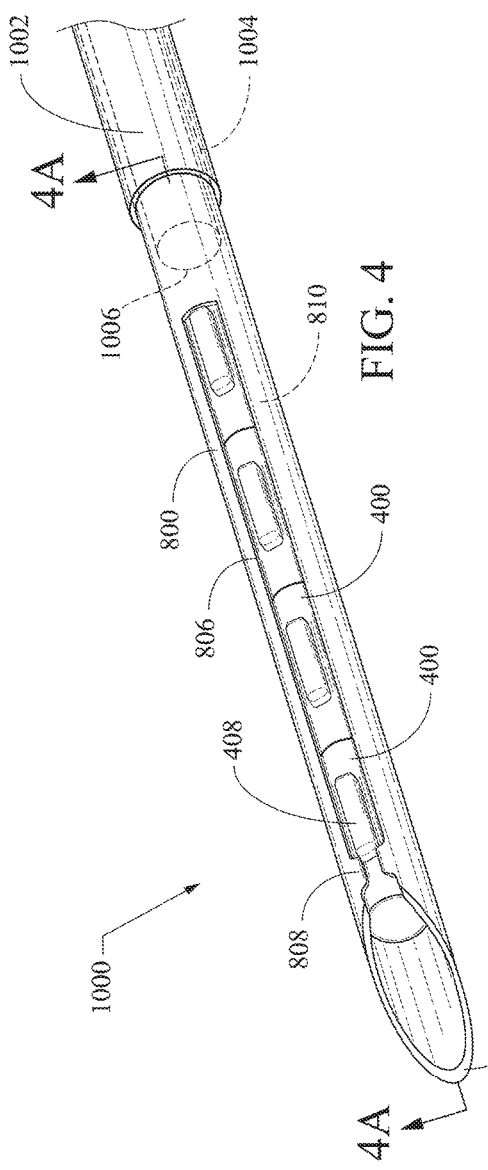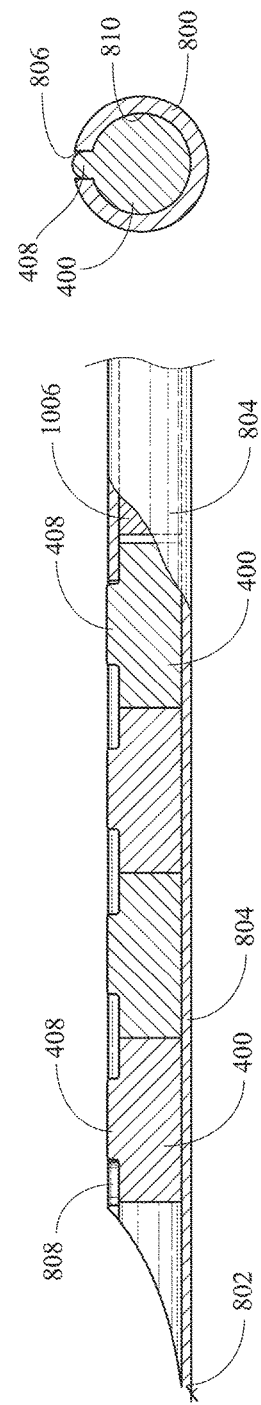
FIG. 4
FIG. 4A
FIG. 4B

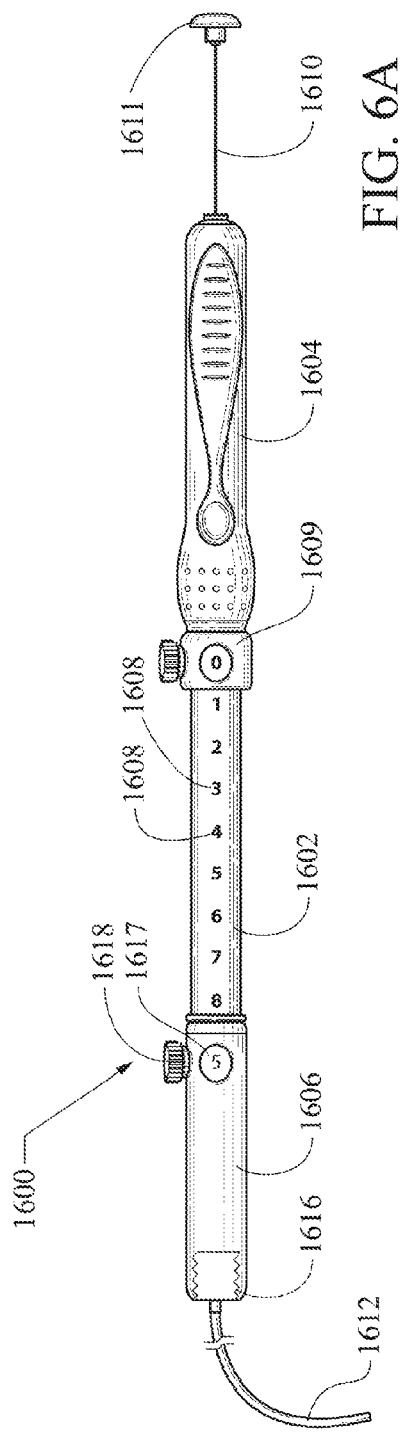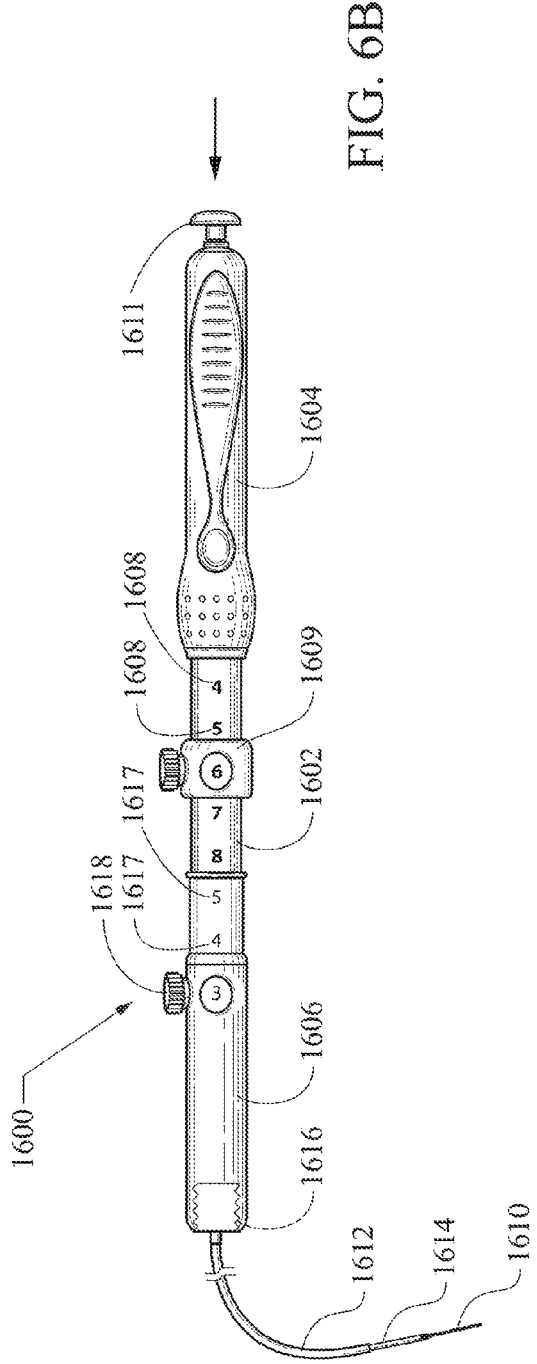

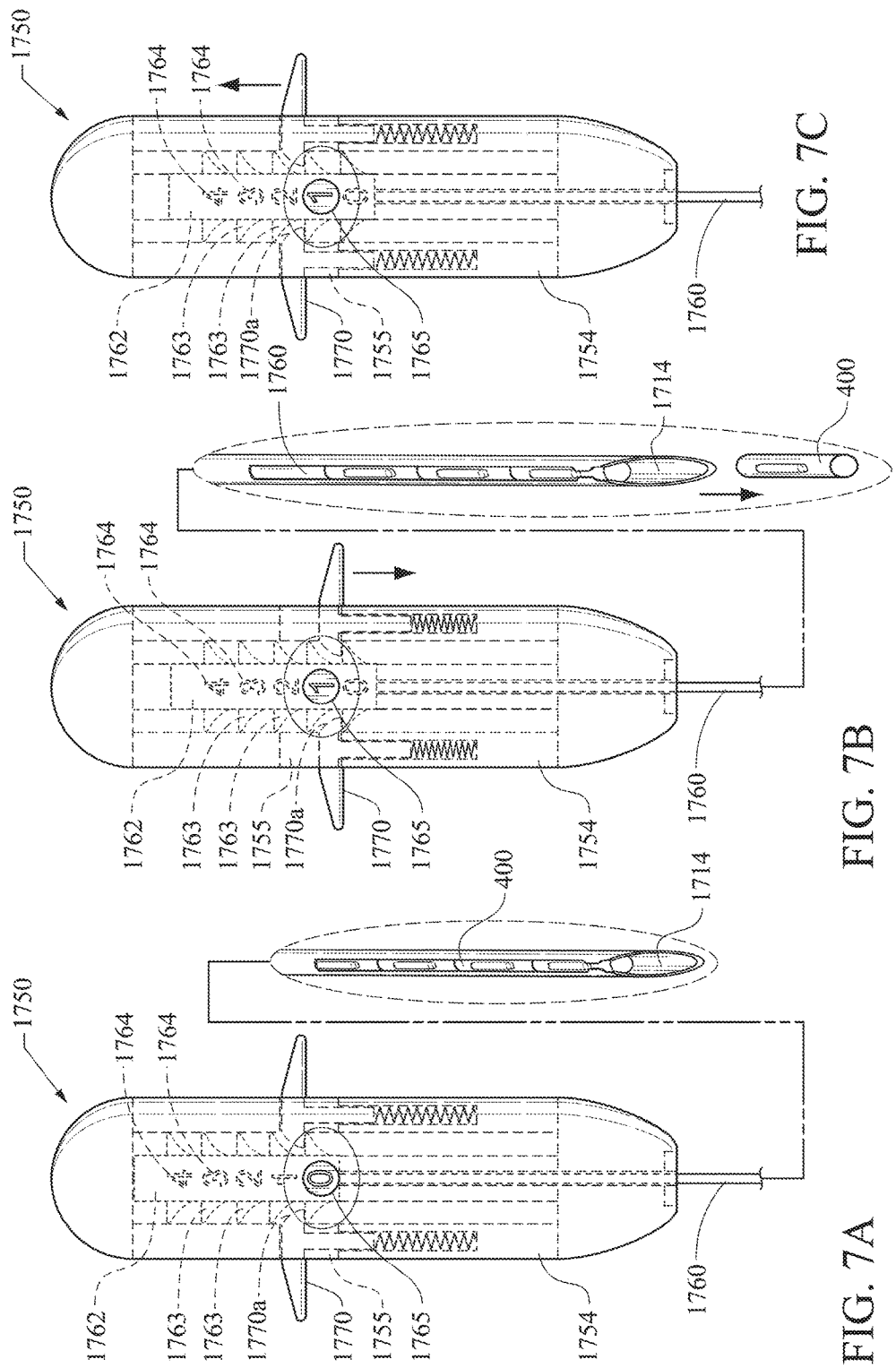

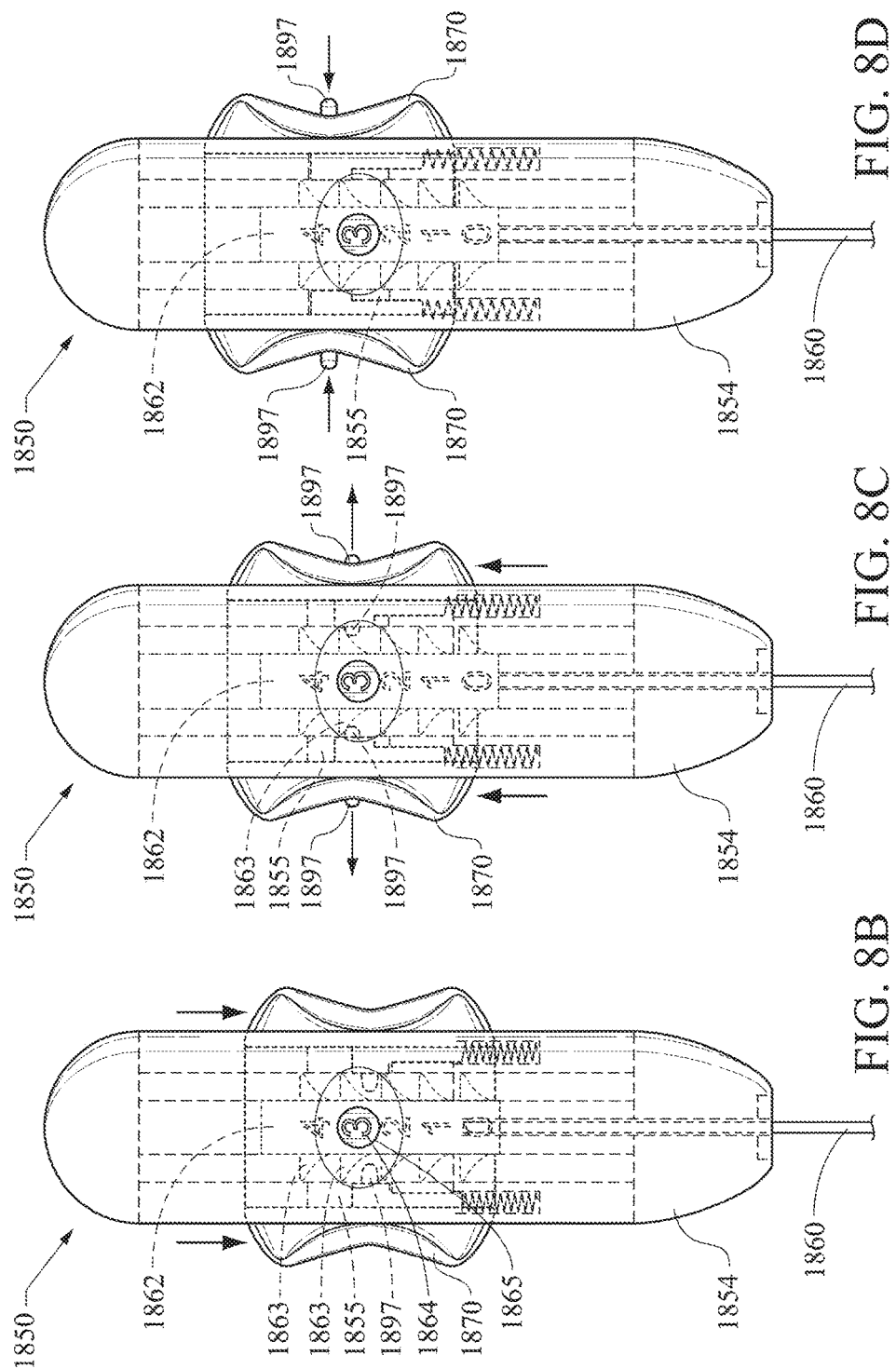

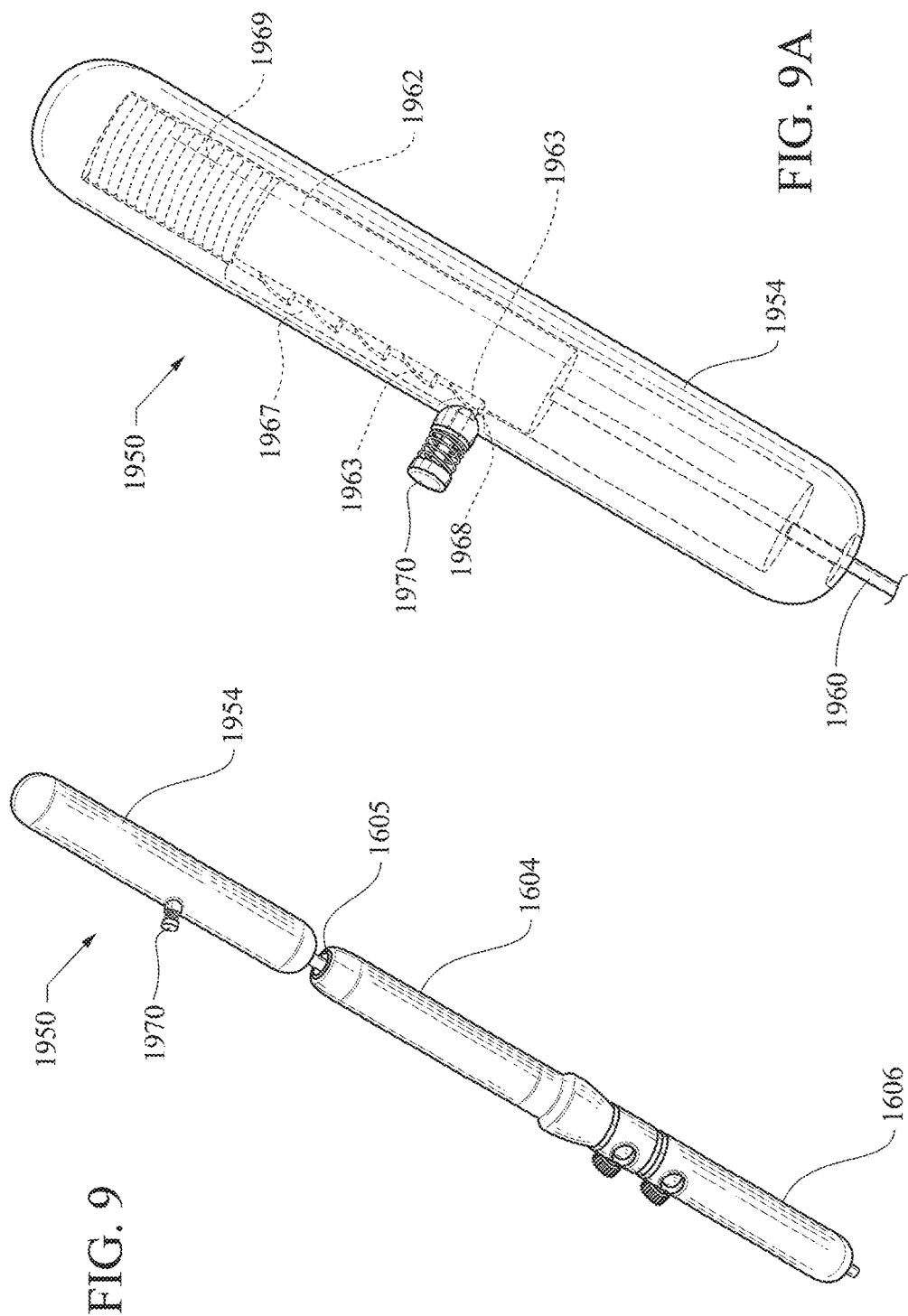

RATCHET-SLIDE HANDLE AND SYSTEM FOR FIDUCIAL DEPLOYMENT

CROSS-REFERENCE TO RELATED APPLICATIONS

This application is a divisional of U.S. patent application Ser. No. 14/180,022, filed Feb. 13, 2014, now U.S. Pat. No. 9,522,264, which claims priority to U.S. provisional application Ser. No. 61/769,295, filed Feb. 26, 2013, each of which is incorporated by reference herein in its entirety.

TECHNICAL FIELD

Embodiments disclosed herein relate generally to a medical device system including one or more fiducials and methods of use for same. More particularly, the disclosed embodiments pertain to handle mechanisms and systems including same for endoscopically deploying fiducials, and methods of use for same.

BACKGROUND

Medical procedures often require locating and treating target areas within a patient. Focused, dose-delivery radiation therapy requires locating the target with a high degree of precision to limit damaging healthy tissue around the target. It is particularly important to know or estimate the precise location of the target in radiation oncology because it is desirable to limit the exposure of adjacent body parts to the radiation in a patient already suffering the depredations of cancer. However, in all treatment procedures, whether radiologic or otherwise, it is most desirable to be able to accurately target a region to be treated.

In many applications, it is not possible to directly view a treatment target or portion thereof (such as, for example, a cancerous tumor, cyst, pseudocyst, or other target) that needs to be acted on in some manner. As one example, when treating a lung or pancreatic tumor with radiation, it may not possible to view the actual tumor within the patient immediately before the radiation treatment. It is therefore highly advantageous to have some mechanism for permitting the tumor to be located accurately so that the radiation treatment can be targeted at the tumor while avoiding damage to healthy tissue.

Even for target regions that may be visualized using CAT (computer-assisted tomography) scans, MRI (magnetic resonance imaging), x-rays, ultrasound, or other techniques, difficulties often arise in targeting a treatment. This is particularly true for target regions within a torso of a patient and soft tissue regions. Due to the mobility of tissues in those regions (e.g., movement of internal organs during respiration and/or digestion, the movement of breast tissue with any change of body position, etc.), a target region may not remain fixed relative to anatomical landmarks and/or to marks that can be placed onto an external surface of a patient's body during one of those visualization procedures.

Several techniques have been developed to address this problem. One such technique is to place markers into the patient along the margins of the target region. The markers may be active (e.g., emitting some kind of signal useful in targeting a therapy) or passive (e.g., non-ferromagnetic metallic markers—called fiducials—that can be used for targeting under ultrasound, MRI, x-ray, or other targeting techniques, which may be included in a treatment device). A fiducial is typically formed of a radio-opaque material that the target can be effectively located and treated with a device that targets a site using the fiducials as positional markers under radiographic detection. Typically, the fiducials may be inserted into the patient during a simple operation. Percutaneous placement is most commonly used. However, use of minimally-invasive placement via an endoscope has recently developed for fiducial placement into a patient's internal organs. For example, percutaneous placement of fiducials along the margins of a pancreatic tumor can be complex and painful (particularly for obese patients, where the needle size is necessarily larger). Another process using percutaneously implanted objects in a patient is brachytherapy. In brachytherapy, radioactive sources or "seeds" are implanted into and/or adjacent a tumor to provide a high dose of radiation to the tumor, but not the healthy tissue surrounding the tumor.

FIGS. 1A and 1B show longitudinal sectional views of a two-piece introducer 100 of the prior art useful for placement of brachytherapy seeds or fiducials. Referring first to FIG. 1A, the introducer 100 includes a needle 102 and a stylet 104 slidably disposed within the needle 102. The stylet 104 includes a first handle 101 and a blunt distal end 106. The needle 102 includes a second handle 103 and a bevel-tipped cannula 108 extending through the second handle 103. The cannula 108 is configured to hold a seed/fiducial 110. The cannula 108 has a distal tip 105 configured for percutaneous implantation of the seed/fiducial 110 into the patient.

In a "pre-loaded configuration," the seed/fiducial 110 is retained in the cannula 108 by a plug 112 made from bone wax or other suitable bio-compatible material(s). This is typically accomplished by a "muzzle-loading" technique where the fiducial is placed into the distal needle and then held in place by the bone wax plug. This can present some challenges, as the bone wax plug 112 can be visible as an artifact in the patient, potentially interfering with clear visualization of body structures or treatment devices. With this configuration, the cannula 108 must be withdrawn and reloaded after delivery of each seed/fiducial 110. If the target locations for the fiducials are very far apart, use of a single percutaneous introducer cannula/trocar for multiple introductions of the cannula 108 may not be possible. In such a circumstance, the patient must endure several percutaneous punctures (and the increased attendant risk of infection for each).

To implant the desired arrangement of seeds/fiducials 110 at a target location in a patient, an operator pushes the cannula 108 in a first direction (arrow A) to insert the tip 105 into the patient (typically under fluoroscopic visualization). The operator then pushes the second handle 103 further in the first direction to position the tip 105 at the desired depth within the patient where a seed/fiducial 110 is to be implanted. Throughout this motion, the operator moves the needle 102 and the stylet 104 together as a unit. At the desired depth/location, the operator grasps the first handle 101 with one hand and the second handle 103 with the other hand. Then, the operator holds the first handle 101 stationary while simultaneously sliding the second handle 103 back in a second direction (arrow B) toward the first handle 101. As shown in FIG. 1B, this movement causes the cannula 108 to retract over the seed/fiducial 110 to implant it in the patient. Alternatively, the operator may move the first handle 101 in the first direction (arrow A) while sliding the second handle 103 back in the second direction (arrow B). This causes the stylet 104 to push the seeds 110 out of the cannula 108. The procedure is then repeated to place other seeds/fiducials 110. When being used for targeting of radiation therapy, a minimum of three fiducials is typically required.

As will be appreciated from the disclosed structure, after deploying one fiducial, one may alternatively reload the introducer 100 from the proximal end by completely withdrawing the stylet 104, then placing another fiducial into the needle lumen and advancing it therethrough to a second location to which the distal needle tip 105 has been directed (a "breech-loading" technique). Provided that the fiducial target sites are sufficiently close together to allow this technique, it can reduce the number of percutaneous punctures or other access procedures needed to place more than one fiducial. However, it creates a problem for procedures where ultrasound is being used or is to be used in the near-future because it introduces air pockets into the tissue and related fluids. Those air pockets with tissue and/or fluid are echogenic in a manner that can interfere with ultrasound visualization of a target area and/or tools being used to diagnose or treat in/around the area. In some brachytherapy techniques, a series of fiducials may be preloaded into the needle—either separately or connected by a suture or similar device—then placed together in fairly close proximity; however, such a technique typically is not effective for placing three or more fiducials in sufficiently disparate locations to use for targeting a treatment relative to, for example, margins of a tumor. This may also be true for multifiducial systems that rely upon a distal plug to retain fiducials, which are thereafter released freely, in contrast with systems according to the present invention, which are configured for controlled serial release (e.g., one at a time, two at a time, or some other user-controlled retention and release of a pre-determined number of fiducials).

The process is similar when implemented endoscopically in the manner developed rather recently, except that the needle and stylet are of the type known in the art for use through the working channel of an endoscope. One limitation of current endoscopic techniques is the size of fiducial that can be introduced. With the size limitation of endoscope working channels, the largest needle that can typically be used without risking bending, crimping, curving or otherwise damaging a needle (that does not have an internal stylet or other support) during advancement out of the endoscope to an anatomical target is a 19-gauge needle. This limits the size of the fiducial that can be introduced through the needle lumen using current, cylindrical fiducials. The endoscopic technique generally suffers from the same reloading problems as described above. Even though the external percutaneous punctures are not an issue, having to withdraw and reload takes up valuable time and complicates the procedure, potentially requiring additional personnel, whether only the stylet is withdrawn for "breech-loading" or the entire device is withdrawn for "muzzle-loading."

It would be desirable to use ultrasound, and particularly endoscopic ultrasound (EUS) for navigation and placement of fiducials. As such it would be desirable to provide and use the largest possible fiducial that will provide improved echogenicity based on its size and echogenic profile. It would be desirable to provide multiple fiducials in a needle that can be introduced in a controlled serial manner (one, or some other pre-determined number, at a time) rather than requiring manual reloading after placement of each fiducial.

BRIEF SUMMARY

Embodiments of a fiducial deployment system described herein may include one or more of: one or a plurality of fiducials having one or more protuberances, a slotted needle configured for delivering a plurality of fiducials in serial fashion where the slot receives the fiducial protuberances without a detent that occupies any internal diameter needle lumen portion, a handle configured for controlling the serial delivery by user-operated deployment of a predetermined number of fiducials, and a method of delivering fiducials to a target region.

BRIEF DESCRIPTION OF THE DRAWINGS

FIGS. 2A-2C show an embodiment of a fiducial from, respectively, top, side, and transverse section views;

FIG. 3 shows a top view of a slotted needle embodiment;

FIG. 3A shows a top view of another slotted needle embodiment;

FIGS. 4-4B show, respectively, a top perspective view, a longitudinal section view, and a transverse section view of a distal fiducial deployment system portion;

FIGS. 6A-6B show a handle embodiment for a fiducial deployment system with actuation of same;

FIGS. 8 and 8A-8D show, respectively, an assembled view, a "see-through view" of FIG. 8, and three actuation method step views, of an advancement mechanism embodiment for a fiducial deployment system; and FIGS. 9 and 9A-9D show, respectively, an external view, an internal-component view, and three method-of-use/function actuation step views of an advancement mechanism embodiment for a fiducial deployment system.

DETAILED DESCRIPTION

Figure 1A:
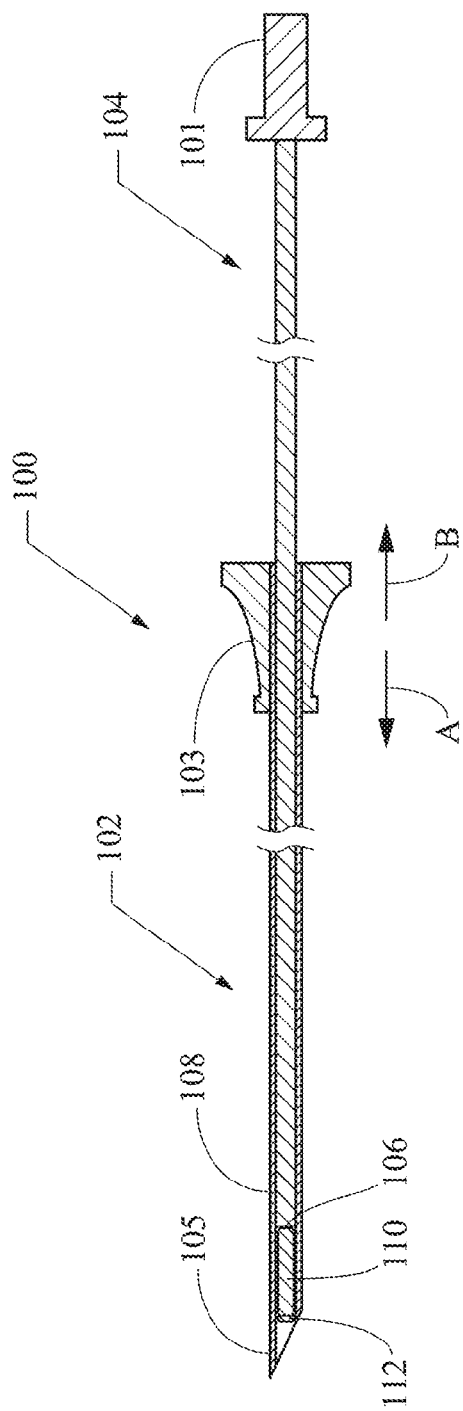
FIGS. 1A-1B show a prior art fiducial introducer and method of use.
Figure 1B:
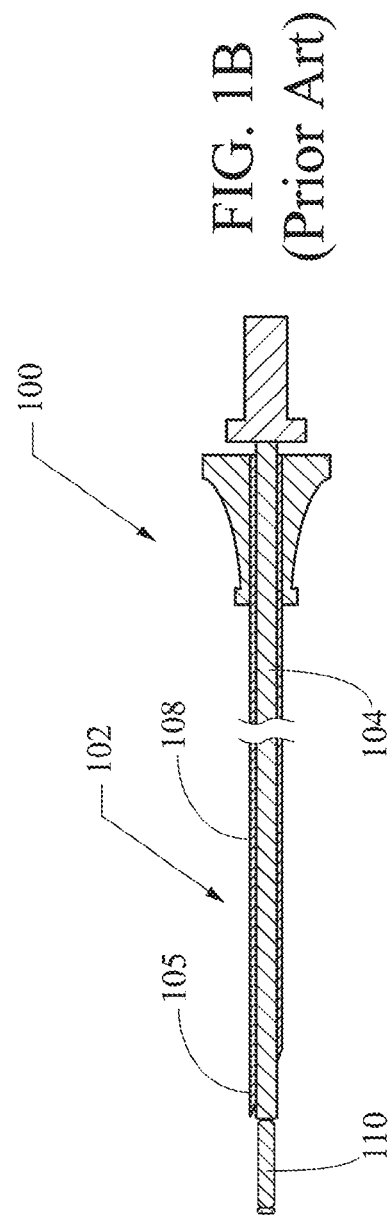

The terms "proximal" and "distal" are used herein in the common usage sense where they refer respectively to a handle/doctor-end of a device or related object and a tool/patient-end of a device or related object.

A variety of fiducial and needle configurations may be used in keeping with the present embodiments including those described in U.S. Pat. App. Publ. Nos. 2010/0280367; 2011/0152611 to Ducharme et al.; 2013/0006101 to McHugo et al.; 2013/0006286 to Lavelle et al.; and 2013/0096427 to Murray et al., each of which is incorporated by reference herein in its entirety. One embodiment, illustrated with reference to FIGS. 2A-2C, of a fiducial 400 has a generally columnar body that is generally cylindrical with a generally circular transverse cross-section. A longitudinal surface face of the body may be dimpled to enhance its ability to reflect ultrasound waves and thereby provide a desirable echogenic profile. This dimpled characteristic may alternatively be embodied as a different irregular, patterned, or textured surface feature (e.g., knurled, ribbed) that may enhance the echogenicity of the fiducial 400, which will aid in visualizing it during EUS-guided placement, and allow it to be used in ultrasound visualization of a target site being marked by one or more fiducials 400 (e.g., a tumor).

Such a fiducial 400 preferably will be formed of a radio-opaque, non-ferromagnetic material such as, for example, gold, platinum, palladium, iridium, or alloys thereof, with one preferred embodiment including an alloy of palladium with rhenium (advantages of which may include desirable radio-opacity, market-price stability superior to gold, and ultrasound-reflectivity/echogenicity due to density). Being radio-opaque will allow the fiducial to be used in deployment techniques using fluoroscopy, as well as making it detectible/visualizable by radiographic means during a treatment or other procedure where it may be desirable to know the location(s) of one or more fiducials. Being non-ferromagnetic will lessen the likelihood that visualization techniques or other procedures employing magnetic fields such as, for example, MRI, will re-orient or otherwise dislodge a fiducial. Echogenic construction of a fiducial or needle may be enhanced by surface texture, but can also be provided by structural inclusions such as embedded bubbles or beads that provide for a different ultrasound reflectivity than material surrounding them. Fiducials may also be coated with a material (e.g., parylene) configured to reduce backscatter during radiography.

In a preferred embodiment, the fiducial 400 is configured and dimensioned for passage through and release from a needle lumen. For an endoscopic delivery system, the fiducial body 402 (exclusive of the protuberance) preferably will have an outer diameter (OD) of about the same or less than the inner diameter (ID) of a needle lumen, but the OD of the fiducial body preferably will be no greater than the needle ID. As used herein, the OD of the fiducial refers to an imaginary circle (or other geometric shape) whose outermost boundaries all fit within the ID of the needle lumen. In other words, it is preferable that the fiducial is dimensioned to fit slidably into the needle lumen, except the protuberance, which projects into the slot.

The longer body portion distal of the protuberance can help make certain that, during deployment through a needle, a first fiducial distal of this second fiducial will be fully advanced out of the needle before that second fiducial is positioned for deployment, as will be made clearer with reference to FIGS. 7-8B below. Accordingly, in many preferred embodiments, the fiducial protuberance (of the second and successive fiducials) will be nearer its proximal end than its distal end, so that the distal fiducial body portion projects sufficiently distally that it will advance the preceding first fiducial completely out of the needle lumen by the time that the second fiducial is in a position to be deployed (see FIGS. 4A-4C, 7B, 8B, and corresponding text). It should be appreciated that, even if all surfaces of the central fiducial portion 402 and protuberance 408 are generally smooth, the preferred materials forming the fiducial 400 and the presence of the protuberance 408 may provide a desirable echogenic profile that is readily visualizable under ultrasound at a resolution sufficient for locating and/or navigating it in a patient's body.

The fiducial 400 has a generally cylindrical body 402 formed as a mass with a generally circular transverse cross-section along its proximal and distal end sections. A protuberance 408 projects from the longitudinal circumferential face 406 of the fiducial body 402. As viewed from the top, the protuberance 408 is generally obround. The irregular shape and increased surface area (as compared to a typical cylindrical fiducial of the type used in plug-ended systems and/or systems with some type of lumen-occupying detent) preferably enhances the echogenicity of the fiducial, which preferably will already be desirably high due in part to its composition.

The protuberance 408 includes protuberance end faces 407 that may provide one or more of chamfered, filleted, and radiused transition to the outer face 406 of the body 402. The body 402 is generally a right cylinder, but for the protuberance 408. In this embodiment, the protuberance 408 is rounded and substantially parallel to the longitudinal central axis of the fiducial body, and it is about one half the length of the body 402, and it is centered along the body length. In a preferred embodiment, the fiducial 400 is configured and dimensioned for passage through and release from a needle lumen. For an endoscopic delivery system, the fiducial body (exclusive of the protuberance) will have an outer diameter (OD) of about the same or less than the inner diameter (ID) of a needle lumen, but the fiducial body OD preferably will be no greater than the needle ID. The protuberance 408 will engage and ride along through a needle slot.

Dimensions of one exemplary embodiment are also described with reference to FIGS. 2A-2C. In one exemplary embodiment the body 402 is about 0.12 inches (3.05 mm) long and has an OD of about 0.034 inches (0.86 mm). The protuberance 408 is about 0.06 inches (1.5 mm) long and is aligned along a midline of the body. The protuberance 408 projects about 0.008 inches (0.2 mm) above the OD of the body 402 and is about 0.011 inches (0.28 mm) wide. These measurements and proportions may be varied in other embodiments while remaining within the scope of the presently-claimed material. For example, the protuberance may be more distally or proximally located, and may be at an angle relative to the midline such that it partially spirals around the outer surface of the body.

FIG. 2C shows an end view of a transverse section taken along line 2C-2C of FIG. 2A. It shows one embodiment of general proportions of a fiducial body and protuberance of the present system.

FIG. 3 shows an embodiment of a fiducial introduction needle 800. The needle 800 is illustrated with a beveled distal tip 802. Its tubular cannula body 804 includes a longitudinal needle slot 806 along a distal end region of the cannula 804. The slot 806 preferably includes at least one detent including at least one detent surface, and more preferably two detents. The slot 806 is shown as being open through the entire wall of the cannula 804, but it should be appreciated that the slot may extend less than the thickness of the needle wall, such that it is embodied as a groove.

In the embodiment of FIG. 3, the detent is formed as a narrowed portion 807 of the slot 806 between two tabs 808. The tabs 808 are generally trapezoidal, but may have a different geometry in other embodiments. As shown in FIG. 3A, in certain preferred embodiments, the tabs 808 may be located immediately adjacent the distal bevel (e.g., to maximize efficiency of advancing a fiducial past them and out of the needle while minimizing residual overlap of a deployed fiducial with the beveled portion of the distal needle tip). Each of the transitions between the edge 806a of the needle slot 806, the proximal tab edge 808a, central tab edge 808b, and distal tab edge 808c may be cornered (e.g., chamfered or filleted) or rounded (e.g., radiused). The tabs 808 preferably are near the distal end of the slot 806.

The body wall cannula 804 generally circumferentially defines a needle lumen 810 configured to allow sliding passage therethrough of a fiducial such as, for example, a fiducial (e.g., as shown in FIGS. 2A-2C or others that would readily pass through the needle lumen 810, preferably with controllable retention of the fiducial(s) by the tabs 808). The needle may be constructed from a nickel-titanium alloy, cobalt-chromium (CoCr) alloy, stainless steel or any other suitable material. Its tip may have a different geometry than the beveled configuration shown. In an alternative embodiment, the tabs 808 may meet such that they will be forced to flex upward and/or outward to a greater degree to allow passage of a protuberance on a fiducial. And, the outer surface of the needle may be dimpled or otherwise textured to provide enhanced echogenicity.

An exemplary needle embodiment is also described with reference to FIG. 3, which exemplary needle embodiment may be configured and dimensioned for use with the exemplary fiducial embodiment described above with reference to FIGS. 2A-2C. In one such exemplary needle embodiment, the ID of the needle lumen is at least about 0.034 inches (0.86 mm). The OD of the needle is about 0.042 inches (1.07 mm; about 19-gauge), with a wall-thickness of about 0.008 inches (0.2 mm). The slot portion proximal of the tabs is about 0.02 inches (0.5 mm) wide and about 0.42 inches (about 10.7 mm) long. Each of the tabs extends about 0.06 inches (0.15 mm) out of the slot edge and has a slot-facing edge that is about 0.02 inches (0.5 mm) long (not including the proximal and distal angled transitions from the slot edge, which are radiused at about 0.005 inches (0.13 mm)). These measurements and proportions may be varied in other embodiments, including those illustrated herein, while remaining within the scope of the presently-claimed material. For example, the particular dimensions of a slot, tabs, and fiducial may be configured for use with a 22-gauge needle having a desirable balance of flexibility and stiffness, as well as including a distal needle tip bevel of about 30°, a slot width of about 0.014 inches (about 0.36 mm) with slot tabs separated only by about 0.006 inches (about 0.15 mm) across the slot, and echogenicity-enhancing surface dimpling disposed along the needle exterior adjacent and generally parallel with at least a distal length of the slot.

The distal end portion of a fiducial deployment system 1000 is described with reference to FIG. 4, which is an external view, FIG. 4A which is a longitudinal section view taken along line 4A-4A of FIG. 4, using the needle 800 and fiducial 400 described above, and FIG. 4B, which shows a transverse section view along line 4B-4B of FIG. 4A. The system 1000 includes a flexible elongate needle sheath 1002. The needle 800, including a more flexible proximal body portion 820 extends through a sheath lumen 1004. At least one fiducial 400, illustrated here as a plurality of fiducials 400, is disposed slidably removably in a distal region of the needle lumen 810 of the needle's cannular body. The central longitudinal body portion 402 substantially occupies the inner diameter of the needle lumen 810. The protuberance 408 of each fiducial 400 has a height that may be about the same as the thickness of the needle wall, including the slot 806 into which the protuberances 408 project.

The protuberance 408 of the distal-most fiducial 400 is captured against the tabs 808 of the needle 800. A stylet 1006 configured for use as a pusher is disposed through a portion of the needle lumen 810 and preferably is configured for actuation from the proximal end, whereby it can be used to distally advance/push out the fiducials and/or hold them in place as the needle is withdrawn from around them. The presence of the fiducials and stylet in the needle 800 preferably improve its columnar strength reduce the likelihood that it will get bent, crimped, or otherwise damaged as it is navigated through and out of the distal end of an endoscope working channel (not shown).

FIG. 4B shows a transverse section end view of a section of a needle 800 (as in FIG. 3) and a fiducial 400 (as in FIGS. 2A-2C). This view shows the preferred close tolerances and a preferred orientation of the fiducial body relative to the needle lumen 810 and the protuberance 408 relative to the needle slot 806.

Several different handle embodiments may be used to effect advancement and release of one or more fiducials. Certain handle embodiments are described with reference to FIGS. 7A-8B below, including with reference to the structure and method described below with reference to FIGS. 4-4B and 5A-5C.

A method of using the fiducial deployment needle of FIGS. 4-4B is described with reference to FIGS. 5A-5C, with reference to the structures shown in greater detail in FIGS. 4-4B. In a preferred method of use, an endoscope 1100 is provided, including a working channel 1102. In one preferred method, the endoscope is an EUS endoscope including a distal ultrasound array 1104 configured for ultrasound imaging. The endoscope 1100 preferably also includes a video element 1106 (e.g., CCD, optical camera, or other means for optical visualization). The methods below are described with reference to placing fiducials 400 at the margins of a tumor 1152 of a patient's pancreas 1150, such that the needle body will be of sufficient length and navigability (e.g., pushability and flexibility) to perorally be directed through a patient's gastrointestinal tract to a target site, including doing so via a working channel of an endoscope such as a gastric endoscope, colonoscope, anuscope, or other visualization/procedure-assisting device.

Figure 5A:
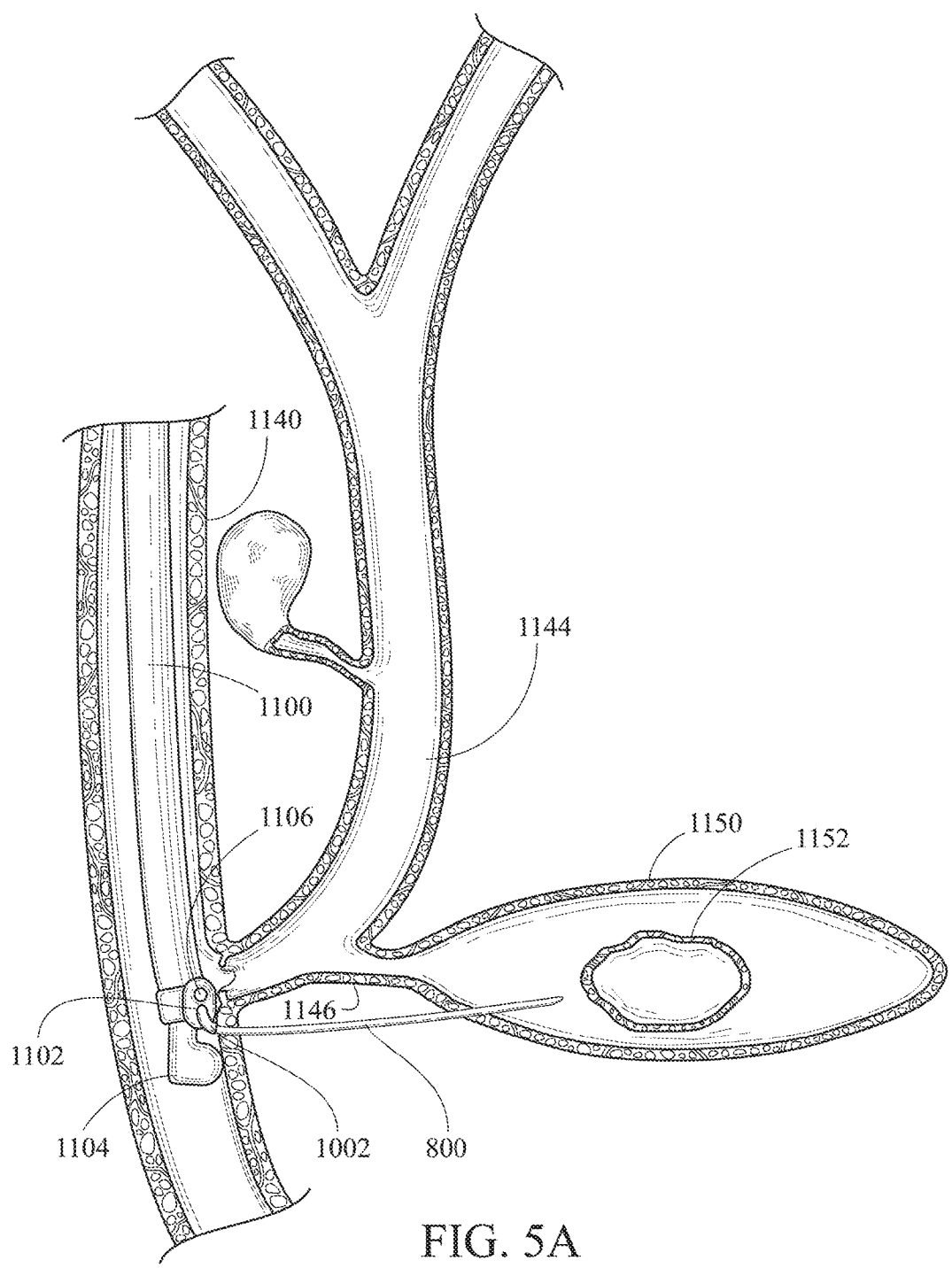
FIGS. 5A-5C show a method of placing fiducials.

The endoscope 1100 is shown in FIG. 5A as having been directed through a patient's duodenum 1140 until its distal end portion is adjacent the Sphincter of Oddi 1142, which provides access to the common bile duct 1144 from which the pancreatic duct 1146 branches and leads to the pancreas 1150.

As shown in FIG. 5A, the sheath 1002 has been advanced to the duodenal wall and the needle 800 has been pierced therethrough, extending near the pancreatic duct 1146 to a location adjacent the tumor 1152 in the pancreas 1150. As shown in FIG. 5B, the needle 800 is directed to a first target site at a margin of the tumor 1152 (preferably under ultrasound guidance, which can be replaced, complemented, and/or verified by fluoroscopy or another visualization technique). Once the distal end 802 of the needle 800 is positioned at the first target, the distal-most fiducial 400 therein is deployed. In one aspect, the deployment may be accomplished by positioning the distal needle end 802 and the fiducial 400 therein at the first target, then retracting the needle 800 while retaining the position of the stylet 1006 such that the fiducial 400 remains in the desired first target position. In another aspect, the deployment may be accomplished by positioning the distal needle end 802 and the fiducial 400 therein adjacent the first target, then holding the needle 800 in position while advancing the stylet 1006 such that the fiducial 400 is advanced into the desired first target position.

As will be appreciated from the structure of the needle 800 and fiducials 400 as shown in FIGS. 4-4B, a user preferably will be able to control advancement/deployment of the fiducials to one at a time, such that a plurality of fiducials (without any spacers) may serially—but separately and independently—directed into different locations. Then the fiducial 400 is in a "ready to deploy" position, its distal protuberance face 408a is engaged against the proximal tab edges 808a. To deploy the fiducial 400, the user must move one of the stylet 1006 or needle 800 relative to the other with sufficient force to advance the protuberance 408 through the tabs 808.

The user preferably will have a tactile sense of resistance as the protuberance 408 passes through the tabs 808, which resistance will decrease immediately as soon as the protuberance clears the tabs. Then the user preferably continues the relative motion of stylet and needle until resistance is again encountered, indicating that the next fiducial behind the distal-most one has met the proximal tab edges 808a.

It will often be preferred that the fiducials (and the protuberances thereon) be proportioned such that complete deployment of a distal-most fiducial includes it substantially clearing the distal needle tip 802 and coincides with the protuberance of the next distal-most fiducial meeting the proximal tab edges 808a. As such, it may be advantageous in some fiducial embodiments to position the protuberance more proximally on the fiducial body such that a fiducial body portion distal of the protuberance is longer than a body portion proximal of the protuberance. It should be appreciated that the protuberance of almost any fiducial embodiment in keeping with principles of the present invention may be disposed near the proximal end up to and including flush with the proximal end of the fiducial body). FIG. 5C shows the fiducial in place, with the needle withdrawn away from it.

Next, the user may retract the needle 800 into the sheath 1002 to a sufficient distance allowing it to be re-extended to a second target site, where the procedure described above may be repeated. These steps may be repeated for placement of third, fourth, and further fiducials. As is known in the art, these fiducials may be used for "positive targeting" and/or "negative targeting" of a therapy such as radiation therapy ("positive targeting" indicating "treat here", and "negative targeting" indicating "do not treat here"). The present system presents numerous advantages. For example, consider a patient already undergoing an endoscopy procedure to biopsy a located but undiagnosed tissue mass. The endoscopic biopsy can be taken and a tissue slide prepared immediately. If a diagnosis is made (in conjunction with whatever other data are available and pertinent) that the tissue mass will benefit from a treatment where placement of fiducials is indicated, the physician can immediately deploy fiducials in the manner described above.

The ability to complete the method using direct/video and ultrasound imaging with little or no use of fluoroscopy presents an advantage of minimizing the radiation exposure of the patient (who may, for example, have to undergo radiation therapies where the total amount of exposure to radiation is desired to be minimized to that which is therapeutically and diagnostically necessary). Advantages of time and expense for the patient, physician and other treating/diagnostic personnel, and the treatment facility are likely as implementation of the present method may prevent all of those entities from having to schedule and conduct a second endoscopic procedure, and/or to extend the initial diagnostic procedure with the time-consuming methods and materials currently available in the prior art as described. It should also be appreciated that, when informed by the present disclosure, those of skill in the art may utilize and/or adapt the presently-disclosed embodiments for percutaneous use while remaining within the scope of one or more claims.

Fiducials with generally cylindrical or otherwise generally regular geometry may migrate after having been placed in a desired location, including that—over the course of multiple treatments of a target area delineated by fiducials—they may migrate with changes in the condition of surrounding tissues. For circumstances where it may be advantageous to minimize migration, a fiducial may be used that includes one or more anchoring projections.

FIGS. 6A-6B show a handle embodiment 1600 that may be used with a fiducial deployment system. The handle 1600 includes a sheath-attached handle member 1602 with a needle-attached handle member 1604 longitudinally slidably disposed on its proximal end. A handle member 1606 (which may be configured for scope-attachment) is slidably attached to the distal end of the sheath-attached handle member 1602. The sheath-attached handle member 1602 is attached to the needle sheath 1612 and the needle-attached handle member 1604 is attached to the needle 1614 (which may be configured in the manner of any of the needles disclosed herein or later developed in accordance with principles of the present disclosure). The scope-attachment handle member 1606 is configured for incrementally fixable, longitudinally-adjustable (relative to the other handle components) attachment to the exterior of an endoscope working channel (not shown) using, for example, a threaded cavity 1616. The scope-attachment handle member 1606 allows a user to determine the distance by which the sheath 1612 will extend from a standard-length endoscope, and it may include numerical or other indicia 1617 corresponding to that relative length and an adjustable engagement structure 1618 allowing a user to select a length and engage the scope-attachment handle member 1606 accordingly. It should be appreciated that embodiments of the handle described and claimed herein may be practiced within the scope of the present invention without including a scope-attachment member.

The sheath-attached handle member 1602 includes numerical indicia 1608 and an adjustable ring 1609 that limits the movement of the needle-attached handle member 1604 and provides a way to select the distance to which the needle 1614 may be extended beyond the sheath 1612. By way of illustration, the configuration shown in FIG. 6A would allow the sheath to extend 5 units (e.g., inches, cm) beyond the distal end opening of an endoscope working channel, and the needle 1614 would not extend at all beyond the distal end of the sheath 1612. The configuration shown in FIG. 6A would allow the sheath to extend 3 units (e.g., inches, cm) beyond the distal end opening of an endoscope working channel, and the needle 1614 would be allowed to extend up to 6 units beyond the distal end of the sheath 1612, although its current position would be only about 4 units beyond the distal end of the sheath 1612.

A stylet 1610 extends through a lumen of the needle 1614 and has a stylet cap 1611 fixed on its proximal end. The stylet 1610 is shown as being retracted proximally in FIG. 6A, and extended beyond the distal end of the needle 1614 in FIG. 6B. The stylet 1610 may be manually advanced distally through the needle lumen in the same manner as described above (with reference to FIGS. 4-4B) for a stylet 1006. As such, a user may use the stylet to manually push fiducials out of a distal end of the needle 1614. If this method is used (e.g., in the manner described above for deployment of fiducials with reference to FIGS. 4-5C), a user may rely upon tactile feedback to determine when a fiducial has been advanced beyond any detents, which may be difficult through a long stylet—particularly if the detents are rounded such that the advancing motion is relatively smooth. Accordingly, it may be advantageous to provide an advancement mechanism configured to attach to (including being integrated with) the handle 1600 that provides improved control of stylet advancement.

Figure 7:
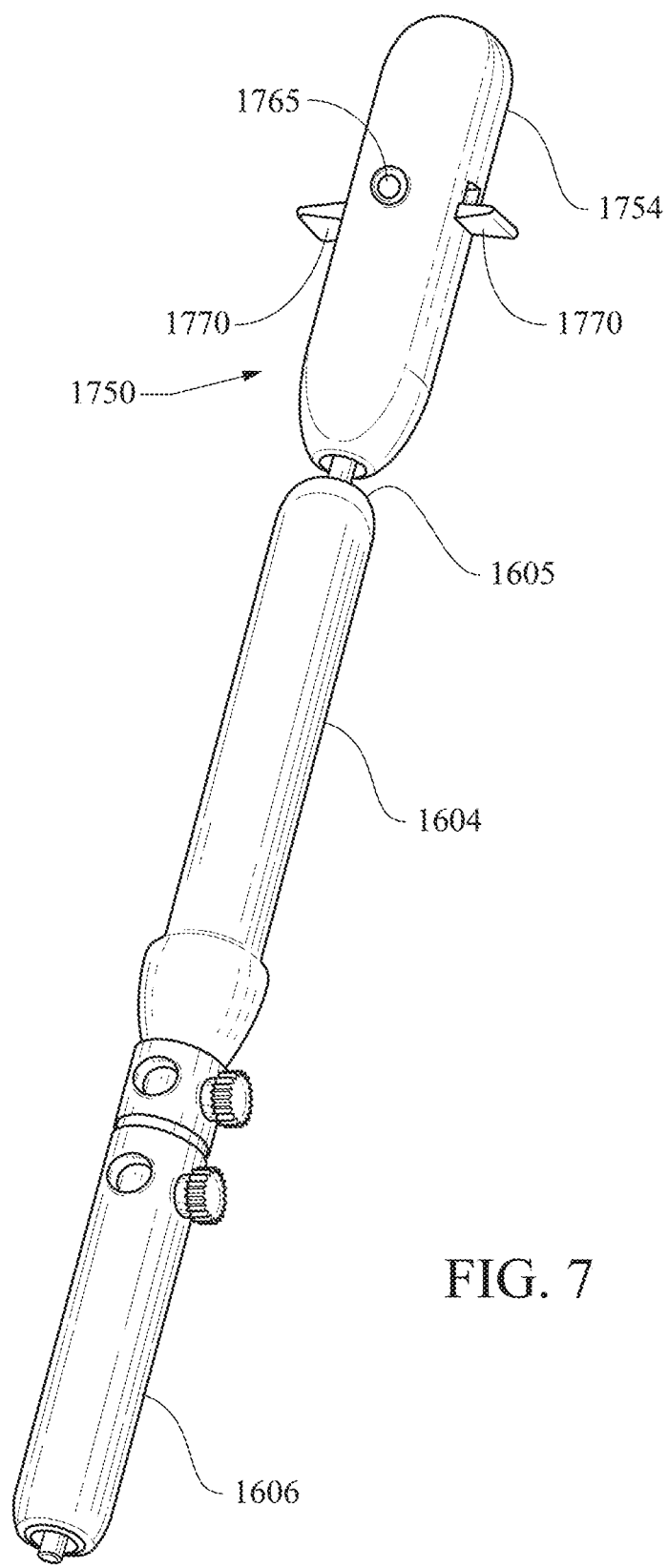
FIGS. 7 and 7A-7C show, respectively, an assembled handle view and three actuation method step views, where each actuation method view is shown corresponding with a distal needle of an advancement mechanism embodiment for a fiducial deployment system, with FIG. 7D showing a longitudinal section view of one actuation method step.
Figure 7D:
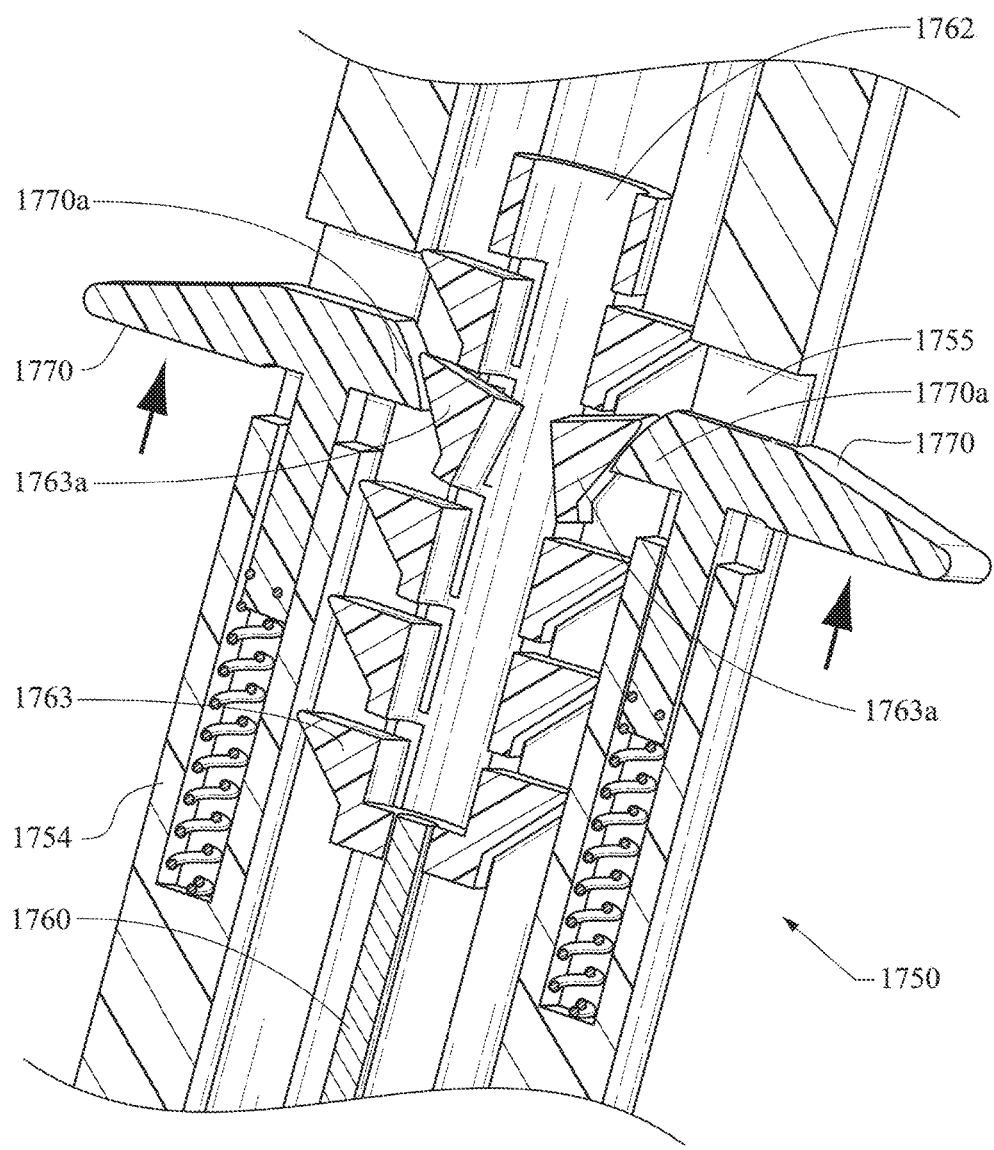

FIGS. 7-9D show embodiments of advancement mechanisms that may be used with handle assembly configurations similar to those of FIGS. 6A-6B, or other handle configurations (including, for example, those disclosed in U.S. Pat. App. Publ. Nos. 2010/0280367; 2011/0152611 to Ducharme et al.; 2013/0006101 to McHugo et al.; 2013/0006286 to Lavelle et al.; and 2013/0096427 to Murray et al. FIGS. 7-7C and 7D show a first ratcheted handle component 1750 for a fiducial deployment system. In this and other embodiments, the first ratcheted component 1750 may be removably or permanently attached to a proximal end 1605 of a handle such as the one shown in FIGS. 6A-6B, where it will provide means for controlled advancement of a stylet (e.g., stylet 1610) in lieu of direct and/or manual manipulation of the stylet cap 1611.

The first ratcheted handle component 1750 may include at least one actuation member 1770 embodied as a slider and an elongate first handle member body 1754 that includes and defines a central longitudinal axis and a handle lumen. It may be attached directly or indirectly to a cannula (e.g., needle and/or sheath), such as via an elongate distal outer body having a longitudinal body lumen (e.g., in some embodiments, needle-attached handle member 1604, or—in other embodiments—a fiducial needle and/or sheath). A stylet 1760 (which may correspond to the stylet 1610) extends through at least a portion of the first handle member 1754 along or generally aligned with its central longitudinal axis.

A rack member 1762 is attached to the proximal stylet end and is longitudinally movably disposed in the lumen of the handle member body 1754. The central rack member 1762 includes a plurality of laterally-protruding ratchet teeth 1763, which are—in this embodiment disposed longitudinally aligned along opposite sides of the rack member. The actuation members—embodied here as two opposed sliders 1770—are each disposed longitudinally slidably in the lumen of the handle member 1754. A user-operable portion of each slider 1770 extends through an aperture 1755 through the handle member wall 1754. The sliders 1770 are biased or urged toward the proximal end by compression coil springs, but those of skill in the art will appreciate that this proximal-directed tendency may be accomplished by a variety of means without exceeding the scope of the present disclosure. The length of the aperture 1755 limits the proximal/distal movement of the sliders 1770, and is dimensioned to correspond to the desired increment of stylet advancement.

As shown in FIGS. 7A-7C, the sliders each include a tooth-engagement portion 1770*a* that extends between adjacent ratchet teeth 1763 on the rack 1762. These figures also show numerical indicia 1764 on the rack 1762, which are visible to a user through a window 1765 in the handle body wall 1754. These indicia (which in other embodiments may be colored bands or other visual indicia) may be used to provide a user with information about the distance advanced by the stylet's distal end from actuation of the sliders 1770. In a fiducial-deployment needle, as contemplated here, the number shown through the window 1765 may indicate the number of fiducials that have been deployed (as the indicia will be spaced apart to correspond with a stylet length advanced to deploy one or another predetermined number of fiducials at/near the distal end region 1714 of an attached fiducial needle, e.g., within a patient body). The rack 1762 may be urged or biased proximally by a spring or other means, a keeper pawl or other keeper structure may be provided (e.g., projecting inward from the handle body wall 1754 in the manner of keeper 1968 below), and/or friction between the stylet and a distal cannula (e.g., needle, sheath, catheter) length may be sufficient, each to prevent retrograde (i.e., proximal) movement of the stylet and rack.

Figure 5B:
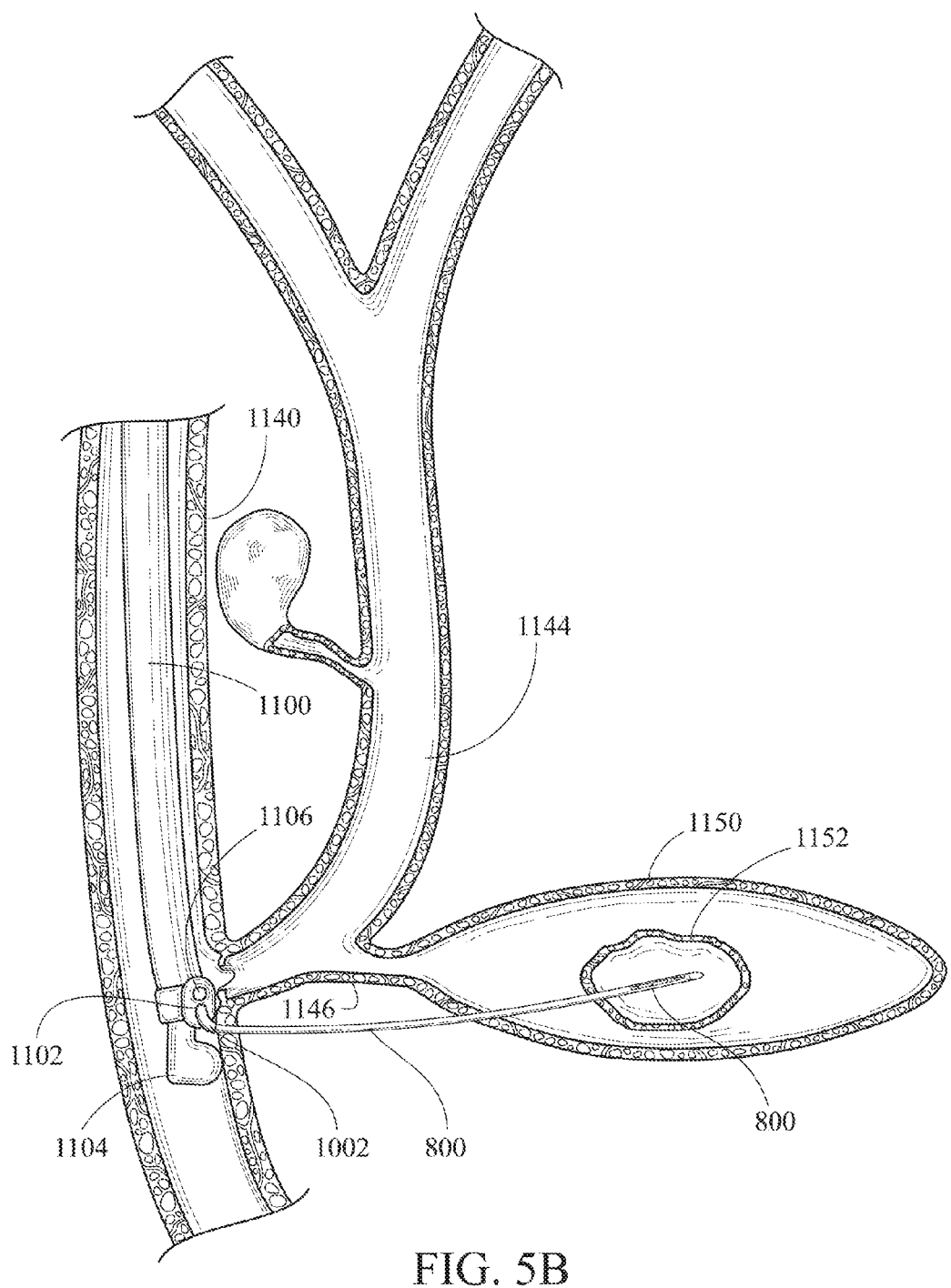
Figure 5C:
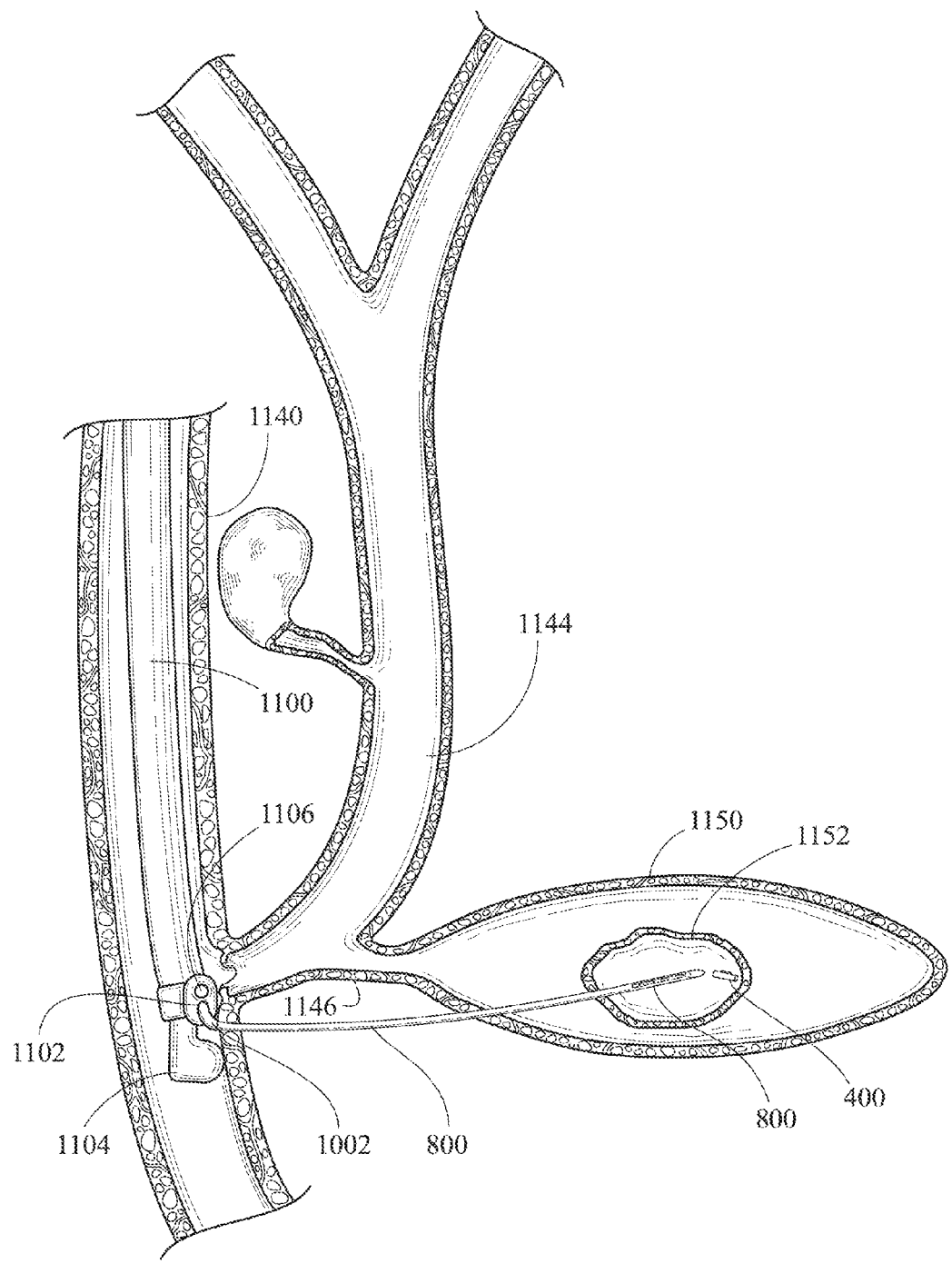

FIGS. 7A-7C show a distal advancement of the rack 1762 and stylet, corresponding to a fiducial-deployment or other distal stylet movement action as shown in an exemplary distal needle view of FIG. 7C (see also, e.g., FIGS. 5B-5C). The longitudinal portion (parallel with the rack) of the sliders may be flexible enough to allow the tooth-engagement portion 1770*a* of the sliders 1770 to bend out of engagement with the teeth 1763. However, one preferred embodiment includes the teeth 1763 being hinged or otherwise retractable and/or depressible (recessible) into the rack 1762, means for which will readily be appreciable by those of skill in the art with reference to the present specification.

This is illustrated with reference to FIG. 7D, showing a longitudinal section view of the rack 1762 in a state during rack-advancement where the teeth 1763 depress, fold back, or are otherwise retracted resiliently into the rack body (e.g., as would occur between the views shown in FIGS. 7B and 7C). The base of each tooth is flexibly attached to the elongate portion of the rack, allowing reciprocal flexing, folding, depression, or the like, with the teeth being biased to the default position shown in FIGS. 7A-7C. Those of skill in the art will appreciate that this can readily be accomplished with polymer and/or memory-metal construction of the rack and teeth, or with other appropriate materials. In this manner, the rack 1762 and/or sliders 1770 are configured to provide unidirectional distal movement of the stylet 1760. The sliders 1770 move reciprocally longitudinally, and the rack 1762 moves distally in a series of discrete predetermined increments that preferably correspond to the distance of stylet movement to deploy/dispense one or some other predetermined number of fiducials. Those of skill in the art will also appreciate with reference to FIGS. 7A-7D and general knowledge of the state of the art that the springs (no reference number) engaged into the distal ends of the sliders 1770 may operate in two different ways: (i) the springs being urged/biased proximally ("expansion biased"), so that the resting/default position of the sliders 1770 is against the proximal end of the apertures 1755 and the sliders 1755 are actuated by distalward movement to deploy a fiducial 400; or (ii) the springs being urged/biased distally ("compression biased"), so that the resting/default position of the sliders 1770 is against the distal end of the apertures 1755 and the sliders 1755 are actuated by proximal slider retraction followed by spring-impelled distalward movement of the sliders against the rack 1762 to deploy a fiducial 400.

Figure 8A:
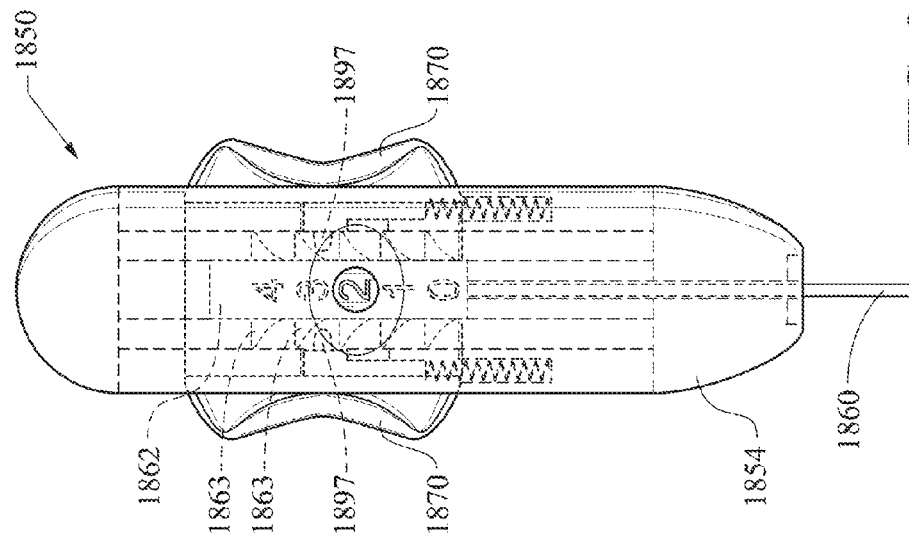
Figure 8:
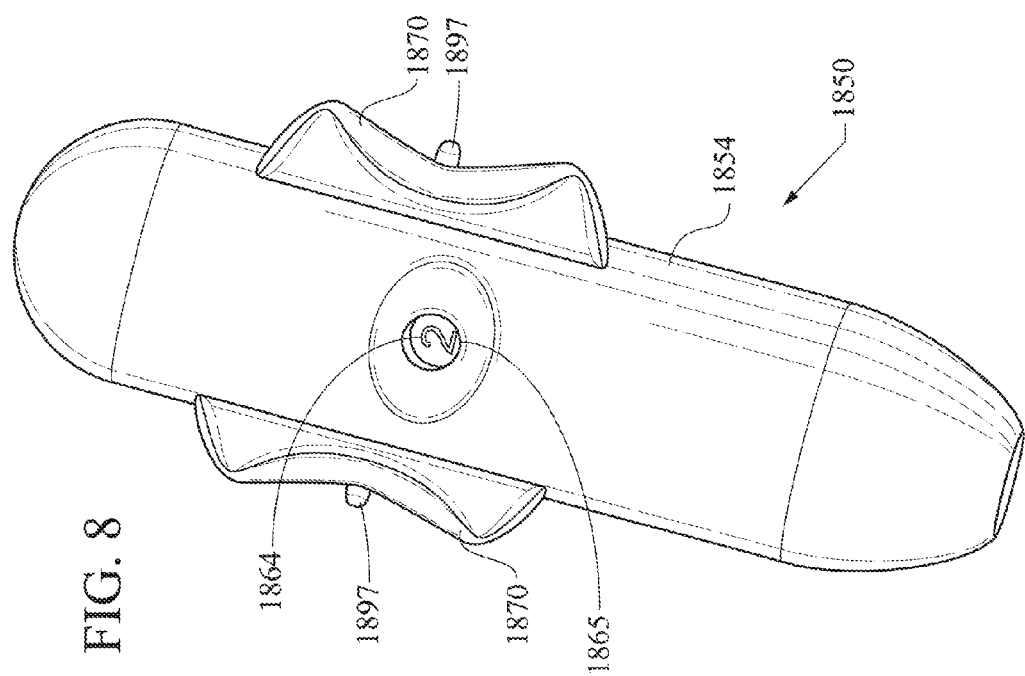

FIG. 8 shows an external view of a second ratcheted handle component 1850 for a fiducial deployment system. In this and other embodiments, the second ratcheted component 1850 may be removably or permanently attached to a proximal end 1605 of a handle such as the one shown in FIGS. 6A-6B, where it will provide means for controlled advancement of a stylet (e.g., stylet 1610) in lieu of direct and/or manual manipulation of the stylet cap 1611. FIGS. 8A-8D show a longitudinal view of internal components, including a method of operation for this embodiment.

The second ratcheted handle component 1850 may include at least one actuation member 1870 embodied as a slider and an elongate first handle member body 1854 that includes and defines a central longitudinal axis and a handle lumen. It may be attached directly or indirectly to a cannula (e.g., needle and/or sheath), such as via an elongate distal outer body having a longitudinal body lumen (e.g., in some embodiments, needle-attached handle member 1604, or—in other embodiments—a fiducial needle and/or sheath). A stylet 1860 (which may correspond to the stylet 1610) extends through at least a distal portion of the first handle member 1854 along or generally aligned with its central longitudinal axis.

A rack member 1862 is attached to the proximal stylet end and is longitudinally movably disposed in the lumen of the handle member body 1854. The central rack member 1862 includes a plurality of laterally-protruding ratchet teeth 1863, which are—in this embodiment disposed longitudinally aligned along opposite sides of the rack member. The actuation members—embodied here as two opposed sliders 1870—are disposed longitudinally slidably through a wall of the handle member 1854. The sliders 1870 are biased or urged toward the proximal end by compression coil springs, but those of skill in the art will appreciate that this proximal-directed tendency may be accomplished by a variety of means without exceeding the scope of the present disclosure.

As shown in FIGS. 8-8D, the sliders each include an actuatable tooth-engagement button 1897 that extends reciprocatingly between adjacent ratchet teeth 1863 on the rack 1862. Each button 1897 is disposed through a user-operable portion of the slider 1870 that extends through an aperture 1855 through the handle member wall 1854. The length of the aperture 1855 limits the proximal/distal movement of the sliders 1870, and is dimensioned to correspond to the desired increment of stylet advancement.

FIGS. 8-8D also show numerical indicia 1864 on the rack 1862, which are visible to a user through a window 1865 in the handle body wall 1854. These indicia (which in other embodiments may be colored bands or other visual indicia) may be used to provide a user with information about the distance advanced by the stylet's distal end from actuation of the sliders 1870. In a fiducial-deployment needle, as contemplated here, the number shown through the window 1865 may indicate the number of fiducials that have been deployed (as the indicia will be spaced apart to correspond with a stylet length advanced to deploy one or another predetermined number of fiducials at the distal end of an attached fiducial needle, e.g., within a patient body). In other embodiments disclosed here or practiced within the scope of the present disclosure, the indicia may show a length/distance (e.g., in cm, percentage of stylet length, or other absolute or relative units), or some other meaningful data. The rack 1862 may be urged or biased distally by a spring or other means, a keeper pawl may be provided, and/or friction between the stylet and a distal cannula (e.g., needle, sheath, catheter) length may be sufficient, each to prevent undesired retrograde (i.e., proximal) movement of the stylet and rack.

FIGS. 8A-8D show steps of a method for distal advancement of the rack 1862 and stylet 1860, corresponding to a fiducial-deployment or other distal stylet movement action (see, e.g., the distal needle end and fiducial deployment shown in FIGS. 5B-5C). As shown in FIG. 8A, the buttons 1897 are biased or urged inward—that is toward, but generally transverse to—the longitudinal axis. In their default position, the buttons 1897 are engaged between and against a proximal face of opposed teeth 1863. A user may advance the sliders 1870 distally to contact the distal end of the aperture 1855, such that the buttons' engagement of the teeth 1863 advances the rack 1862 and stylet distally by the desired increment. Then, as shown in FIG. 8B-8C, the buttons may be released by the user and the sliders may be moved (or they will move by being spring-urged) back proximally. As this occurs, the buttons 1897 will be allowed to reciprocate outward away from the longitudinal axis to pass over the next pair of opposed teeth, behind/proximal of which the buttons will engage (as shown in FIG. 8D) for a potential next actuation.

Stated differently, the sliders 1870 are actuated to move longitudinally, and the buttons engage the teeth so that the rack 1862 moves distally. This may be done reciprocatingly in a series of discrete predetermined increments that preferably correspond to the distance of stylet movement to deploy/dispense one or some other predetermined number of fiducials.

Figure 9B:
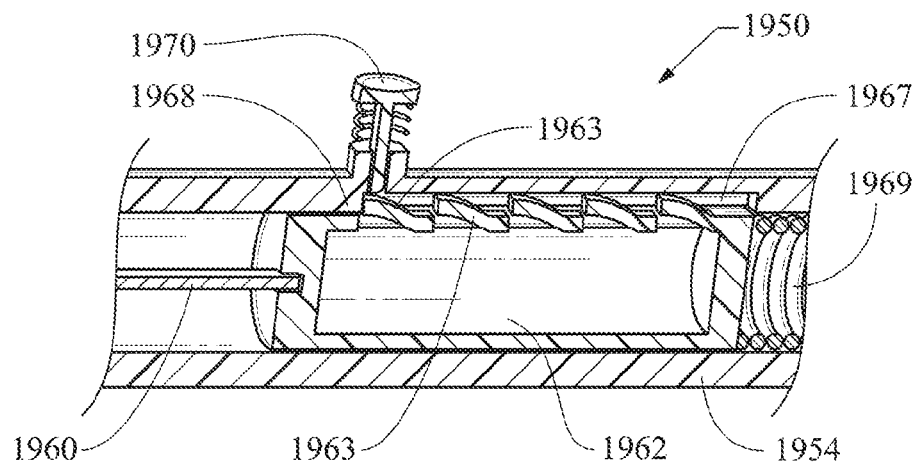
Figure 9C:
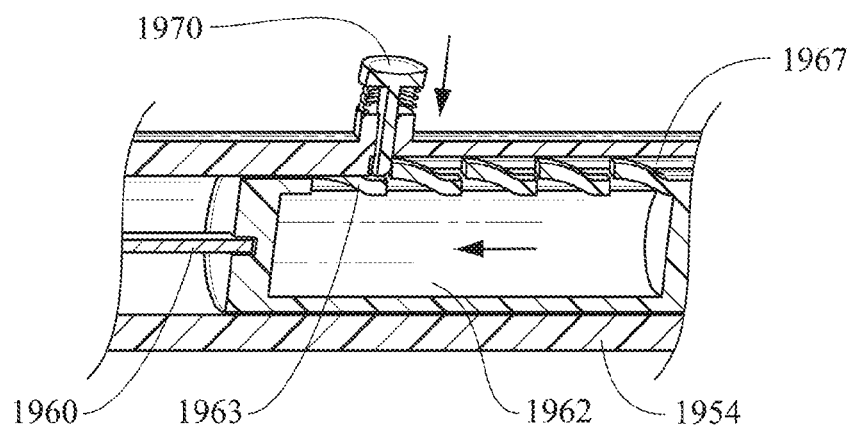
Figure 9D:
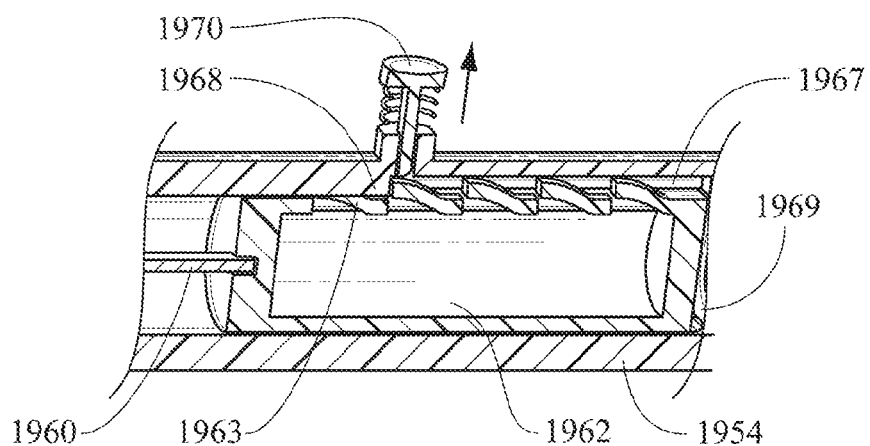

FIGS. 9-9D show a third ratcheted handle embodiment including a handle component 1950 for a fiducial deployment system. In this and other embodiments, the ratcheted component 1950 may be removably or permanently attached to a proximal end 1605 of a handle such as the one shown in FIGS. 6A-6B, where it will provide means for controlled advancement of a stylet (e.g., stylet 1610) in lieu of direct and/or manual manipulation of the stylet cap 1611. FIG. 9 shows an external view of the handle component 1950 in such an assembly. FIGS. 9A-9D show a longitudinal view of internal components, including a method of operation for this embodiment.

As shown in FIGS. 9 and 9A, the handle component 1950 may include an actuation member configured as a depressible button 1970. The button 1970 is disposed reciprocatingly/depressibly through the wall of an elongate first handle member body 1954 that includes and defines a central longitudinal axis and a handle lumen. The handle body 1954 may be attached directly or indirectly to a cannula (e.g., needle and/or sheath), such as via an elongate distal outer body having a longitudinal body lumen (e.g., in some embodiments, needle-attached handle member 1604, or—in other embodiments—a fiducial needle and/or sheath). A stylet 1960 (which may correspond to the stylet 1610) extends through at least a distal portion of the first handle member 1954 along or generally aligned with its central longitudinal axis.

A rack member 1962 is attached to the proximal stylet end and is longitudinally movably disposed in the lumen of the handle member body 1954. The central rack member 1962 includes a plurality of laterally-protruding ratchet teeth 1963, which are—in this embodiment disposed longitudinally aligned along a single side of the rack member 1962. The actuation member—embodied here as the button 1970—is disposed generally transversely through a wall of the handle member 1954 in a manner contacting a face of at least one of the plurality of ratchet teeth 1963. The depressible button 1970 is biased or urged (e.g., by a spring or other means) away from and transverse to the handle longitudinal axis.

As shown in FIGS. 9A-9D, the rack 1962 is urged or biased distally by a spring 1969 or other means. A keeper element 1968 prevents the distal movement of the rack by engaging a distalmost protruding/non-depressed tooth 1963 of the rack 1962. The teeth are depressible into the rack, as shown in the progression of FIGS. 9B-9D. The keeper element 1968 is embodied here by a protrusion of the inner surface of the handle wall 1954. The rack 1962 and the lumen formed within the handle are both generally cylindrical with the outer diameter of the rack (excepting the protruding teeth) being about the same or only slightly less than the inner diameter of the handle 1954 (excepting a recessed track 1967 along which the non-depressed ratchet teeth 1963 are afforded longitudinal passage). The keeper 1968 is formed by a distal end of the recessed track 1967. In other embodiments, the keeper may be embodied as an indentation along the inner handle wall, where only one or some sub-plurality of ratchet teeth are non-depressed, and the distalmost one engages the wall, while all teeth proximal or distal of the indentation/keeper region are depressed by contact with the inner diameter of the handle wall.

With this structure disclosed, those of skill in the art will appreciate a method of use. As shown in FIG. 9B, the button 1970 may be actuated and depressed against a distalmost non-depressed tooth 1963, which (as shown in FIG. 9C) will depress the tooth, disengaging it from retraining contact with the keeper 1968. Thus relieved, the rack-urging spring 1969 advances the rack distally until the next distalmost, non-depressed tooth stoppingly contacts the keeper 1968, as shown in FIG. 9D. Thereafter the procedure may be repeated. The distance between keeper-engaging surfaces of successive teeth 1963 preferably is dimensioned to correspond to the desired increment of stylet advancement (e.g., for distal deployment of one or a predetermined number of fiducials).

As with the foregoing embodiments, a handle window and numerical or other indicia (not shown) may be provided to show the increment or degree to which the rack has been advanced. Those of skill in the art will appreciate that actuation may user-perceptibly be indexed by visual indicia, tactile indicia, audible indicia, or any combination thereof, and that the indicia may be configured to correspond to a pre-determined longitudinal movement distance of the stylet by the rack(s). A variety of such indicia are known and well within the skill in the art, given the present disclosure.

Those of skill in the art will appreciate with reference to the embodiments disclosed above that a predetermined number of fiducials may be released into a desired location by a single actuation of the lever, button, or other actuation member. The predetermined number preferably will be one, but may include a plurality of fiducials. The configuration of the present embodiments provide clear advantages over prior designs that utilize releasable end-plugs in a needle to retain fiducials, and/or that use less refined means of controlling the fiducial release than the notch/tab needle design and/or actuation handles described herein.

Drawings and particular features in the figures illustrating various embodiments are not necessarily to scale. Some drawings may have certain details magnified for emphasis, and any different numbers or proportions of parts should not be read as limiting, unless so-designated by one or more claims. Those of skill in the art will appreciate that embodiments not expressly illustrated herein may be practiced within the scope of the present invention, including that features described herein for different embodiments may be combined with each other and/or with currently-known or future-developed technologies while remaining within the scope of the claims presented here. For example, a needle and fiducials of the present system may be used percutaneously, including in another minimally invasive surgical procedure, such as a laparoscopic-type procedure, within the scope of the claimed invention. For example, a target site may be a location in or near the gastrointestinal tract (e.g., liver, pancreas) such as those locations that may be accessible by endoscopy (using a minimally invasive endoscope introduced through a natural patient orifice, e.g., mouth, anus, vagina). This includes—more broadly—sites reachable through NOTES (natural orifice translumenal endoscopic surgery) procedures. The present method and device may also be used with other minimally-invasive surgical techniques such as percutaneous endoscopic procedures (e.g., laparoscopic procedures) or percutaneous non-endoscopic procedures, but most preferably is used with less invasive endoscopy procedures. It is therefore intended that the foregoing detailed description be regarded as illustrative rather than limiting. And, it should be understood that the following claims, including all equivalents, are intended to define the spirit and scope of this invention.

We claim:

1. A medical device handle configured for controlled incremental lengthwise stylet advancement through a cannula, the handle comprising:
    an elongate outer handle body defining a longitudinal handle lumen;
    an elongate cannula attached directly or indirectly to a distal end of the handle body, the cannula defining a longitudinal cannula lumen in mechanical communication with the handle lumen;
    a rack member, including a plurality of longitudinally-aligned, laterally protruding and depressible, retractable, and/or foldable teeth, where the rack member is disposed within the handle lumen;
    a stylet extending distally from the rack member into the cannula lumen; and
    a pair of actuation members with a portion of the actuation members engaging against one of or between two or more of the plurality of teeth, where actuating of the actuation members by moving the actuation members longitudinally relative to the handle along a handle slot of predetermined length is effective to move the rack member distally by a predetermined lengthwise increment.

2. The medical device handle of claim 1, where the predetermined lengthwise increment corresponds to a length of a fiducial.

3. The medical device handle of claim 1, where the actuation members are urged proximally.

4. The medical device handle of claim 1, where the rack member includes indicia, viewable through a window in the handle member, of a number of fiducials deployed by distalward movement of the rack member relative to the cannula.

5. The medical device handle of claim 1, where the actuation members are configured as generally symmetrical sliders.

6. The medical device handle of claim 1, where the rack member and the elongate outer handle body each are generally cylindrical with an outer diameter of the rack member—exclusive of the teeth—about the same or slightly less than an inner diameter of the handle lumen, and where the inner diameter of the handle lumen includes a recessed track allowing longitudinal movement of teeth of the rack member, and a portion of the recessed track comprises a keeper element.

7. The medical device handle of claim 1, where the rack member teeth, the actuation members, or both, are configured for unidirectional distal rack-advancing engagement when the actuation members are moved distally, and are configured to allow non-rack-moving proximal reciprocation of the actuation members from a proximal handle slot end toward a distal handle slot end.

8. The medical device handle of claim 1, where the rack member teeth flex out of a longitudinal linear axis in toward a longitudinal central axis of the rack member when contacted by the actuation members.

9. The medical device handle of claim 1, where the rack member is generally longitudinally hollow along at least a lengthwise portion including the rack member teeth.

10. The medical device handle of claim 1, where the rack member teeth each is generally shaped as a right triangle.

11. The medical device handle of claim 1, where the base of each rack member tooth is flexibly attached to an elongate portion of the rack member, providing for reciprocal flexing, folding, or depression, with the teeth being biased to a default position aligned with a longitudinal axis of the rack member.

* * * * *